(12) United States Patent
Sasaki

(10) Patent No.: US 10,867,367 B2
(45) Date of Patent: *Dec. 15, 2020

(54) IMAGE PROCESSING APPARATUS, IMAGE PROCESSING METHOD, COMPUTER-READABLE RECORDING MEDIUM, AND ENDOSCOPE APPARATUS

(71) Applicant: OLYMPUS CORPORATION, Tokyo (JP)

(72) Inventor: Hiroshi Sasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 33 days.

This patent is subject to a terminal disclaimer.

(21) Appl. No.: 15/587,921

(22) Filed: May 5, 2017

(65) Prior Publication Data

US 2017/0243325 A1    Aug. 24, 2017

Related U.S. Application Data

(63) Continuation of application No. PCT/JP2014/080684, filed on Nov. 19, 2014.

(51) Int. Cl.
*A61B 1/04* (2006.01)
*H04N 9/07* (2006.01)
(Continued)

(52) U.S. Cl.
CPC ........ *G06T 3/4007* (2013.01); *A61B 1/00009* (2013.01); *A61B 1/04* (2013.01);
(Continued)

(58) Field of Classification Search
CPC . A61B 1/00009; A61B 1/0638; A61B 1/0646; A61B 1/04; A61B 1/05;
(Continued)

(56) References Cited

U.S. PATENT DOCUMENTS 5,552,827 A    9/1996    Maenaka et al.
8,531,512 B2    9/2013    Gono et al.
(Continued)

FOREIGN PATENT DOCUMENTS

JP    H07-236147 A    9/1995
JP    2005-333418 A    12/2005
(Continued)

OTHER PUBLICATIONS

Wu et al. , Improvement of Color Video Demosaicking in Temporal Domain: Oct. 2006 (Year: 2006).*
(Continued)

*Primary Examiner* — Dave Czekaj
*Assistant Examiner* — Samuel D Fereja
(74) *Attorney, Agent, or Firm* — Scully, Scott, Murphy & Presser, P.C.

(57) ABSTRACT

An image sensor includes first and second pixels to generate a first electric signal from white illumination light and second electric signals from narrow band illumination light, respectively. Density of the first pixels is higher than density of each color components of the second pixels. An image processing apparatus is configured to: interpolate the first electric signal based on the first pixels surrounding the second pixels to generate an interpolated electric signal; calculate a difference between the interpolated electric signal and the second electric signals to generate a color difference signal; discriminate an interpolation direction based on the color difference signal to interpolate a missing color difference signal at each pixel position, thereby generating an interpolated color difference signal; and generate the second electric signals to be generated by the second pixels, based on the interpolated color difference signal and the interpolated electric signal.

7 Claims, 17 Drawing Sheets

(51) Int. Cl.
  *G06T 3/40* (2006.01)
  *A61B 1/00* (2006.01)
  *G02B 23/24* (2006.01)
  *A61B 1/06* (2006.01)
  *H04N 5/225* (2006.01)
  *G02B 26/00* (2006.01)

(52) U.S. Cl.
  CPC ........ *A61B 1/0638* (2013.01); *G02B 23/2484* (2013.01); *H04N 5/2256* (2013.01); *H04N 9/07* (2013.01); *G02B 26/008* (2013.01); *H04N 2005/2255* (2013.01); *H04N 2209/044* (2013.01); *H04N 2209/046* (2013.01)

(58) Field of Classification Search
  CPC ....... A61B 1/043; A61B 1/00186; A61B 1/00; A61B 1/045; A61B 1/0669; A61B 5/0084; A61B 1/00045; A61B 5/0071; A61B 1/051; A61B 1/063; A61B 1/0684; A61B 1/06; A61B 1/07; A61B 1/00006; A61B 1/0653; A61B 1/0661; A61B 1/0005; A61B 1/00059; A61B 1/00013; A61B 1/00096; A61B 1/005; A61B 1/2733; A61B 5/0075; A61B 1/0002; A61B 1/00126; A61B 1/00165; A61B 1/00172; A61B 1/0052; A61B 1/018; A61B 1/041; A61B 5/0077; A61B 5/0086; A61B 5/14546; A61B 5/1455; A61B 5/4872; A61B 5/742; A61B 1/00016; A61B 1/00057; A61B 1/00112; A61B 1/00114; A61B 1/00163; A61B 1/015; A61B 1/042; A61B 1/0676; A61B 5/14551; A61B 5/1459; A61B 5/489; H04N 2005/2255; H04N 5/2256; H04N 9/045; H04N 9/07; H04N 7/18; H04N 9/04; H04N 2209/044; H04N 2209/046; H04N 5/232; H04N 5/372; H04N 2209/048; H04N 5/225; H04N 5/2252; H04N 5/2258; H04N 5/33; H04N 5/335; H04N 5/3452; H04N 5/347; H04N 5/353; H04N 5/378; H04N 7/183; H04N 9/09; H04N 9/097; H04N 9/12; H04N 9/67; H04N 9/77; H04N 2209/043; H04N 5/217; H04N 5/2254; H04N 5/2257; H04N 5/23209; H04N 5/23245; H04N 5/2354; H04N 5/238; H04N 5/243; H04N 5/332; H04N 9/077; H04N 9/083; H04N 9/64; H04N 9/643; G02B 23/2484; G02B 23/2461; G02B 23/24; G02B 23/2469; G02B 23/2476; G02B 23/2423; G02B 23/2438; G02B 26/008; G02B 5/201; G02B 5/22; G06T 3/4015; G06T 7/0012; G06T 2207/10024; G06T 2207/10068; G06T 2207/30101; G06T 2207/20036; G06T 7/11; G06T 7/90; G06T 11/60; G06T 2200/24; G06T 2207/20182; G06T 2207/20192; G06T 2207/20221; G06T 2207/30024; G06T 3/4007; G06T 5/002; G06T 5/50; G06T 7/0014; G06T 1/00; G06T 1/0007; G06T 2207/10152; G06T 2207/20212; G06T 2207/30092; G06T 5/20; A61L 31/00165
  See application file for complete search history.

(56) References Cited

U.S. PATENT DOCUMENTS

| | | | |
|---|---|---|---|
| 2009/0066821 A1* | 3/2009 | Achong | H04N 9/045 348/273 |
| 2011/0176730 A1 | 7/2011 | Sasaki | |
| 2014/0111673 A1 | 4/2014 | Hayashi | |
| 2015/0092032 A1* | 4/2015 | Kuramoto | A61B 1/00059 348/68 |

FOREIGN PATENT DOCUMENTS

| | | |
|---|---|---|
| JP | 2006-068113 A | 3/2006 |
| JP | 2011-143100 A | 7/2011 |
| JP | 5456206 B2 | 3/2014 |

OTHER PUBLICATIONS

International Search Report dated Feb. 24, 2015 issued in PCT/JP2014/080684.

* cited by examiner

FIG.3

| $P_{11}$ | $P_{12}$ | $P_{13}$ | $P_{14}$ | ... |
|---|---|---|---|---|
| $P_{21}$ | $P_{22}$ | $P_{23}$ | $P_{24}$ | ... |
| $P_{31}$ | $P_{32}$ | $P_{33}$ | $P_{34}$ | ... |
| $P_{41}$ | $P_{42}$ | $P_{43}$ | $P_{44}$ | ... |
| ⋮ | ⋮ | ⋮ | ⋮ | ⋱ |

| $R_{11}$ | $G_{12}$ | $R_{13}$ | $G_{14}$ | ... |
|---|---|---|---|---|
| $G_{21}$ | $B_{22}$ | $G_{23}$ | $B_{24}$ | ... |
| $R_{31}$ | $G_{32}$ | $R_{33}$ | $G_{34}$ | ... |
| $G_{41}$ | $B_{42}$ | $G_{43}$ | $B_{44}$ | ... |
| ⋮ | ⋮ | ⋮ | ⋮ | ⋱ |

FIG.9

| $(B-G)_{11}$ |  | $(B-G)_{13}$ |  | ... |
|---|---|---|---|---|
|  | $(R-G)_{22}$ |  | $(R-G)_{24}$ | ... |
| $(B-G)_{31}$ |  | $(B-G)_{33}$ |  | ... |
|  | $(R-G)_{42}$ |  | $(R-G)_{44}$ | ... |
| ⋮ | ⋮ | ⋮ | ⋮ | ⋱ |

FIG.10

|  | B-G (k,l-2) |  | B-G (k+2,l-2) |
|---|---|---|---|
| B-G (k-1,l-1) |  | B-G (k+1,l-1) |  |
|  | B-G (k,l) |  | B-G (k+2,l) |
| B-G (k-1,l+1) |  | B-G (k+1,l+1) |  |

FIG.19

| B-G (k-1,l-1) | | B-G (k+1,l-1) |
|---|---|---|
| (B-G)p (k-1,l) | | (B-G)p (k+1,l) |
| B-G (k-1,l+1) | | B-G (k+1,l+1) |

FIG.20

| B-G (k-1,l-1) | (B-G)p (k,l-1) | B-G (k+1,l-1) |
|---|---|---|
| | | |
| B-G (k-1,l+1) | (B-G)p (k,l+1) | B-G (k+1,l+1) |

FIG.21

| B-G (k-1,l-1) |              | B-G (k+1,l-1) |
|---------------|--------------|---------------|
|               | (B-G)p (k,l) |               |
| B-G (k-1,l+1) |              | B-G (k+1,l+1) |

FIG.22

| B-G (k-1,l-1)   | (B-G)p (k,l-1) | B-G (k+1,l-1)   |
|-----------------|----------------|-----------------|
| (B-G)p (k-1,l)  | (B-G)p (k,l)   | (B-G)p (k+1,l)  |
| B-G (k-1,l+1)   | (B-G)p (k,l+1) | B-G (k+1,l+1)   |

IMAGE PROCESSING APPARATUS, IMAGE PROCESSING METHOD, COMPUTER-READABLE RECORDING MEDIUM, AND ENDOSCOPE APPARATUS

CROSS REFERENCES TO RELATED APPLICATIONS

This application is a continuation of PCT international application Ser. No. PCT/JP2014/080684, filed on Nov. 19, 2014 which designates the United States, incorporated herein by reference.

BACKGROUND

1. Technical Field

The disclosure relates to an image processing apparatus, an image processing method, and a computer-readable recording medium for performing signal processing on an imaging signal generated by an image sensor to generate an image signal. The disclosure also relates to an endoscope apparatus including the image processing apparatus.

2. Related Art

Conventionally, endoscope apparatuses have been widely used for various kinds of examinations in a medical field and an industrial field. Among such endoscope apparatuses, a medical endoscope apparatus is capable of acquiring an in-vivo image inside a body cavity even without cutting a subject by inserting a flexible insertion portion, which is provided with an image sensor including a plurality of pixels at a distal end thereof and formed in an elongated shape, into the body cavity of the subject such as a patient. Thus, the medical endoscope apparatus imposes a light burden on the subject, and has been widely used.

As an observation method of such an endoscope apparatus, white light imaging using white illumination light having a white color (white illumination light) and narrow band imaging using illumination light having a narrow band, which is a wavelength band narrower than a white wavelength band (narrow band illumination light) have been already widely known. Among these, the narrow band imaging can obtain an image, for example, in which capillaries, mucosal fine patterns, and the like, present in a mucosal superficial portion of a living body (living body surface layer), are highlighted. According to the narrow band imaging, it is possible to more accurately found a lesion region in the mucosal superficial portion of the living body. In regard to these observation methods of the endoscope apparatus, there is a demand to perform observation by switching between the white light imaging and the narrow band imaging.

As a method of performing observation by switching between the white light imaging and the narrow band imaging, endoscope systems have been proposed that are capable of switching between a white light imaging mode in which a tissue inside a body cavity is irradiated with illumination light of three primary colors of R, G and B, sequentially to generate a white illumination light observation image using the reflected light, and a narrow band imaging mode in which the tissue inside the body cavity is irradiated with beams of light having two narrow bands included, respectively, in wavelength bands of blue light and green light, sequentially to generate a narrow band light observation image from the reflected light (for example, see JP 2006-68113 A). Beams of light having two narrow bands included, respectively, in wavelength bands of blue light and green light, are different from each other in terms of absorption characteristics of hemoglobin in blood vessel and an attenuation amount in depth direction of the living body depending on the wavelength. In a special light observation image, it is possible to capture a capillary of a surface layer and a mucosal structure of the surface layer using the narrow band light included in the wavelength band of blue light, and a thicker blood vessel of a deep layer using the narrow band light included in the wavelength band of the green light.

In order to generate and display a color image using the above-described observation method, a color filter configured by arraying filters that pass light of red (R), green (G), green (G) and blue (B) wavelength bands, respectively, as a single filter unit (unit) for each pixel, which is generally called the Bayer array, is provided on a light receiving surface of an image sensor so as to acquire a captured image using the single-plate image sensor. In this case, each pixel receives light of a wavelength band having passed through the filter and generates an electric signal of a color component corresponding to the light of the wavelength band. Thus, interpolation processing to interpolate a signal value of a color component that has been missed without passing through the filter in each pixel is performed in the process of generating the color image. Such interpolation processing is called demosaicing processing. Hereinafter, a signal acquired by a G pixel (a pixel in which a G filter is arranged, similar definition is applied for an R pixel and a B pixel) will be referred to as a G signal (an R signal in the case of the R pixel and a B signal in the case of the B pixel).

As an example of the demosaicing processing, disclosed is a technique of interpolating G signals in R and B pixels where the G signals are missed, using correlations with surrounding G pixels thereof, and interpolating a color difference signal by performing interpolation processing on color difference signals (an R-G signal and a B-G signal), calculated using an R signal of the R pixel or a B signal at the B pixel position, at a pixel position where the color difference signal is missed, using the correlations with the surrounding G pixels, which has been used in interpolating the G signal (for example, see JP 2005-333418 A).

SUMMARY

In some embodiments, provided is an image processing apparatus for generating an image signal based on electric signals output from an image sensor, the image sensor including first pixels and second pixels, the first pixels and the second pixels being arranged in a matrix, the first pixels being configured to perform photoelectric conversion on received light to generate an electric signal of a first luminance component as a luminance component of white illumination light, the white illumination light including red wavelength band light, green wavelength band light and blue wavelength band light, the second pixels being configured to perform photoelectric conversion on received light to generate electric signals of color components including a second luminance component as a luminance component of narrow band illumination light, the narrow band illumination light having a narrower wavelength band than wavelength bands of the white illumination light, and density of the first pixels being higher than density of each of the color components of the second pixels. The image processing apparatus includes: an interpolated color difference calculation unit configured to: interpolate the electric signal of the first luminance component based on the electric signal of the first pixels surrounding the second pixels at positions of the second pixels to generate an interpolated electric signal of the first luminance component; and calculate a difference between the interpolated electric signal of the first luminance component and the electric signals of the color components generated by the second pixels to generate a color difference signal; a color difference interpolation unit configured to discriminate an interpolation direction based on the color difference signal generated by the interpolated color difference calculation unit to interpolate a missing color difference signal at each pixel position, thereby generating an interpolated color difference signal; and an image signal generation unit configured to generate the electric signals of the color components to be generated by the second pixels, based on the interpolated color difference signal generated by the color difference interpolation unit and the interpolated electric signal of the first luminance component generated by the interpolated color difference calculation unit.

In some embodiments, provided is an image processing method for generating an image signal based on electric signals output from an image sensor, the image sensor including first pixels and second pixels, the first pixels and the second pixels being arranged in a matrix, the first pixels being configured to perform photoelectric conversion on received light to generate an electric signal of a first luminance component as a luminance component of white illumination light, the white illumination light including red wavelength band light, green wavelength band light and blue wavelength band light, the second pixels being configured to perform photoelectric conversion on received light to generate electric signals of color components including a second luminance component as a luminance component of narrow band illumination light, the narrow band illumination light having a narrower wavelength band than wavelength bands of the white illumination light, and density of the first pixels being higher than density of each of the color components of the second pixels. The image processing method includes: interpolating the electric signal of the first luminance component based on the electric signal of the first pixels surrounding the second pixels at positions of the second pixels to generate an interpolated electric signal of the first luminance component, and calculating a difference between the interpolated electric signal of the first luminance component and the electric signals of the color components generated by the second pixels to generate a color difference signal; discriminating an interpolation direction based on the color difference signal to interpolate a missing color difference signal at each pixel position, thereby generating an interpolated color difference signal; and generating the electric signals of the color components to be generated by the second pixels, based on the interpolated color difference signal and the interpolated electric signal of the first luminance component.

In some embodiments, provided is a non-transitory computer-readable recording medium with an executable program stored thereon for generating an image signal based on electric signals output from an image sensor, the image sensor including first pixels and second pixels, the first pixels and the second pixels being arranged in a matrix, the first pixels being configured to perform photoelectric conversion on received light to generate an electric signal of a first luminance component as a luminance component of white illumination light, the white illumination light including red wavelength band light, green wavelength band light and blue wavelength band light, the second pixels being configured to perform photoelectric conversion on received light to generate electric signals of color components including a second luminance component as a luminance component of narrow band illumination light, the narrow band illumination light having a narrower wavelength band than wavelength bands of the white illumination light, and density of the first pixels being higher than density of each of the color components of the second pixels. The program causes a computer to execute: interpolating the electric signal of the first luminance component based on the electric signal of the first pixels surrounding the second pixels at positions of the second pixels to generate an interpolated electric signal of the first luminance component, and calculating a difference between the interpolated electric signal of the first luminance component and the electric signals of the color components generated by the second pixels to generate a color difference signal; discriminating an interpolation direction based on the color difference signal to interpolate a missing color difference signal at each pixel position, thereby generating an interpolated color difference signal; and generating the electric signals of the color components to be generated by the second pixels, based on the interpolated color difference signal and the interpolated electric signal of the first luminance component.

In some embodiments, an endoscope apparatus includes: a light source unit configured to emit white illumination light or narrow band illumination light, the white illumination light including red wavelength band light, green wavelength band light and blue wavelength band light, and the narrow band illumination light having a narrower wavelength band than wavelength bands of the white illumination light; an image sensor that includes first pixels and second pixels, the first pixels and the second pixels being arranged in a matrix, the first pixels being configured to perform photoelectric conversion on received light to generate an electric signal of a first luminance component as a luminance component of the white illumination light, the second pixels being configured to perform photoelectric conversion on received light to generate electric signals of color components including a second luminance component as a luminance component of the narrow band illumination light, and density of the first pixels being higher than density of each of the color components of the second pixels; and the image processing apparatus.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a schematic diagram illustrating a configuration of a pixel of an image sensor according to the first embodiment of the present invention;

FIG. 4 is a schematic diagram illustrating an exemplary configuration of a color filter according to the first embodiment of the present invention;

FIG. 9 is a schematic diagram for describing demosaicing processing performed by a processor according to the first embodiment of the present invention;

FIG. 10 is a schematic diagram for describing demosaicing processing performed by a processor according to the first embodiment of the present invention;

FIG. 19 is a schematic diagram for describing demosaicing processing performed by the processor according to the second embodiment of the present invention;

FIG. 20 is a schematic diagram for describing the demosaicing processing performed by the processor according to the second embodiment of the present invention;

FIG. 21 is a schematic diagram for the describing demosaicing processing performed by the processor according to the second embodiment of the present invention;

FIG. 22 is a schematic diagram for describing another example of the demosaicing processing performed by the processor according to the second embodiment of the present invention.

DETAILED DESCRIPTION

Hereinafter, modes for carrying out the present invention (hereinafter, referred to as "embodiment(s)") will be described. In the embodiments reference will be made to a medical endoscope apparatus that includes an image processing apparatus according to the present invention and captures and displays an image inside a body cavity of a subject such as a patient. The invention is not limited by the embodiments. The same reference signs are used to designate the same elements throughout the drawings.

Although a part of a wavelength band of white light will be referred to as a "narrow band" in the following embodiments, the narrow band may be a wavelength band in a narrower range than the wavelength band of the white light. Alternatively, the narrow band may include a wavelength band (for example, infrared, ultraviolet, and the like) outside the range of the wavelength band of the white light (visible light).

First Embodiment

Figure 1:
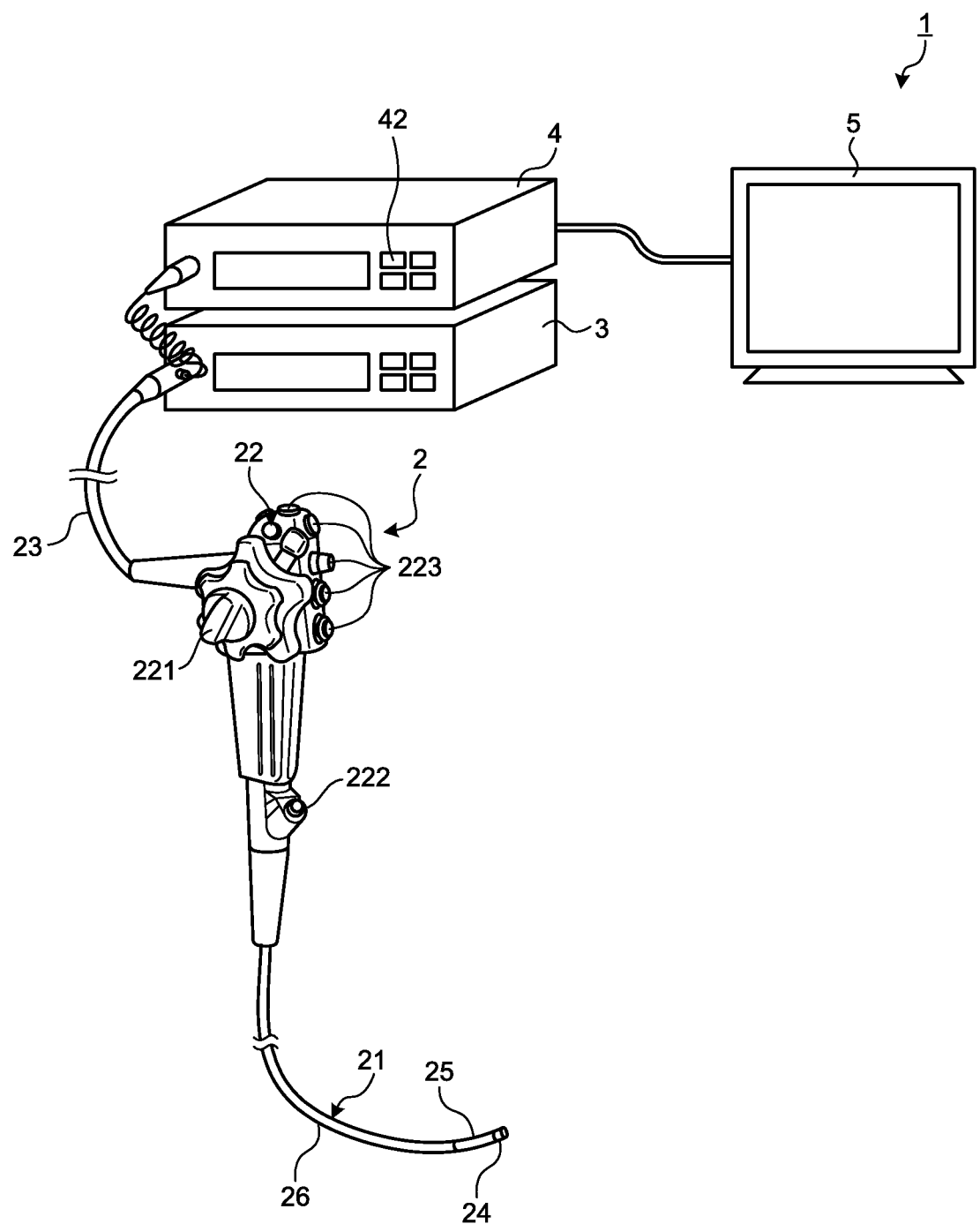
FIG. 1 is a diagram illustrating a schematic configuration of an endoscope apparatus according to a first embodiment of the present invention.
Figure 2:
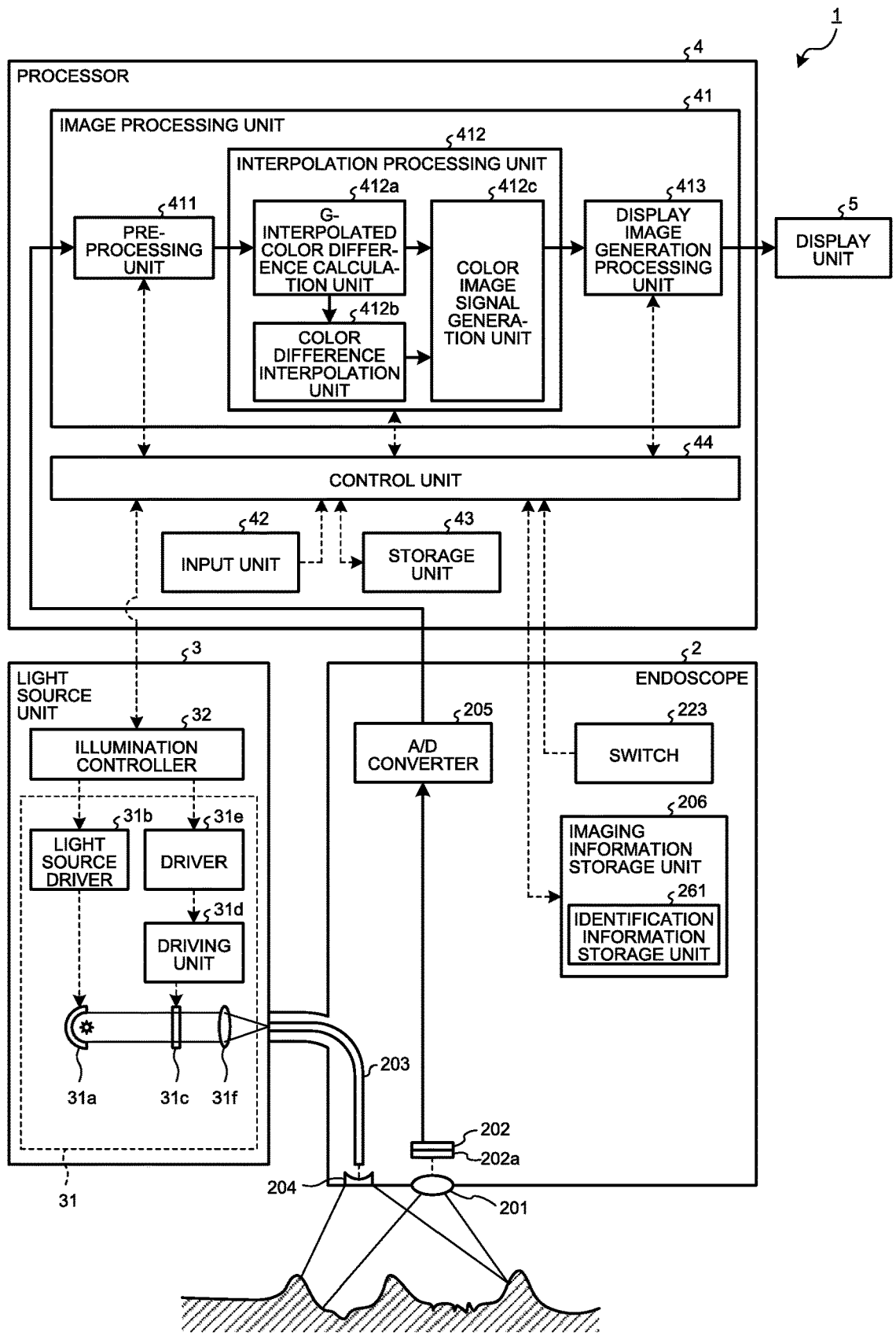
FIG. 2 is a schematic diagram illustrating a schematic configuration of the endoscope apparatus according to the first embodiment of the present invention.

FIG. 1 is a diagram illustrating a schematic configuration of an endoscope apparatus according to a first embodiment of the present invention. FIG. 2 is a schematic diagram illustrating a schematic configuration of the endoscope apparatus according to the first embodiment. An endoscope apparatus 1 illustrated in FIGS. 1 and 2 includes: an endoscope 2 that captures an in-vivo image of an observed region by inserting an insertion portion 21 into a body cavity of a subject and generates an electric signal; a light source unit 3 that generates illumination light to be emitted from a distal end of the endoscope 2; a processor 4 that performs predetermined image processing on the electric signal acquired by the endoscope 2 and integrally controls the entire operation of the endoscope apparatus 1; and a display unit 5 that displays the in-vivo image having been subjected to the image processing by the processor 4. The insertion portion 21 of the endoscope apparatus 1 is configured to be inserted into the body cavity of the subject such as a patient to acquire the in-vivo image of the body cavity. A user such as a doctor observes the acquired in-vivo image to examine presence or absence of a bleeding site or a tumor site (lesion site S), which is a detection target region.

The endoscope 2 includes: the insertion portion 21 that has flexibility and an elongated shape; an operating unit 22 that is connected to a proximal end side of the insertion portion 21 and receives input of various kinds of operation signals; and a universal cord 23 that extends from the operating unit 22 in a direction different from an extending direction of the insertion portion 21 and includes various types of built-in cables which are connected to the light source unit 3 and the processor 4.

The insertion portion 21 includes: a distal end portion 24 that includes a built-in image sensor 202 in which pixels (photodiodes) to receive light are arrayed in a lattice shape (in a matrix) and which generates an image signal by performing photoelectric conversion on the light received by the pixels; a bending portion 25 that is bendable and has a plurality of bending pieces; and an elongated flexible tube portion 26 that is connected to a proximal end side of the bending portion 25 and has flexibility.

The operating unit 22 includes: a bending knob 221 for bending the bending portion 25 in an up-and-down direction and a right-and-left direction; a treatment tool insertion portion 222 through which a treatment tool such as biopsy forceps, an electrical scalpel, or a test probe is inserted into the body cavity of the subject; and a plurality of switches 223 to receive a command signal to cause the light source unit 3 to perform a switching operation of illumination light, an operation command signal for an external device that is connected to the treatment tool and the processor 4, a water feed command signal to feed water, a suction command signal to perform suctioning, and the like. The treatment tool is configured to be inserted from the treatment tool insertion portion 222 and is projected from an opening (not illustrated) via a treatment tool channel (not illustrated) which is provided at a distal end of the distal end portion 24.

At least a light guide 203 and a cable assembly formed by assembling one or a plurality of signal lines are built in the universal cord 23. The cable assembly is the signal line to transmit and receive signals among the endoscope 2, the light source unit 3, and the processor 4, and includes a signal line to transmit and receive setting data, a signal line to transmit and receive an image signal, a signal line to transmit and receive a drive timing signal to drive the image sensor 202, and the like.

In addition, the endoscope 2 includes an imaging optical system 201, an image sensor 202, a light guide 203, an illumination lens 204, an A/D converter 205, and an imaging information storage unit 206.

The imaging optical system 201 is provided at the distal end portion 24 and collects light at least from an observed region. The imaging optical system 201 is configured using one or a plurality of lenses. The imaging optical system 201 may include an optical zooming mechanism to change a viewing angle and a focusing mechanism to change a focal point.

The image sensor 202 is provided perpendicularly to an optical axis of the imaging optical system 201, performs photoelectric conversion on an image of light formed by the imaging optical system 201, and generates an electric signal (image signal). The image sensor 202 is implemented using a charge coupled device (CCD) image sensor, a complementary metal oxide semiconductor (CMOS) image sensor, and the like.

FIG. 3 is a schematic diagram illustrating a configuration of a pixel of the image sensor according to the first embodiment. The image sensor 202 includes a plurality of pixels which receive light from the imaging optical system 201 arrayed in a lattice shape (in a matrix). Further, the image sensor 202 generates an electric signal (also referred to as an imaging signal or the like) formed by performing photoelectric conversion on the light received by each pixel. This electric signal includes a pixel value (luminance value) of each pixel and position information of pixels, and the like. In FIG. 3, a pixel which is arranged at i-th row and j-th column is denoted as a pixel $P_{ij}$.

The image sensor 202 includes a color filter 202a that is provided between the imaging optical system 201 and the image sensor 202 and includes a plurality of filters each of which is configured to pass light having individually set wavelength bands. The color filter 202a is provided on a light receiving surface of the image sensor 202.

FIG. 4 is a schematic diagram illustrating an exemplary configuration of the color filter according to the first embodiment. The color filter 202a is configured by arranging filter units U1, formed using four filters arrayed in a 2×2 matrix, to be arrayed in a matrix in accordance with arrangement of the pixels $P_{ij}$. In other words, the color filter 202a is configured by arranging basic patterns repeatedly, using a filter array of the filter units U1 as the basic pattern. The single filter, which passes light of a predetermined wavelength band, is arranged on each light receiving surface of the respective pixels. Thus, the pixel $P_{ij}$, provided with the filter, receives light of a wavelength band that pass through the corresponding filter. For example, the pixel $P_{ij}$ that is provided with the filter that passes light of a green wavelength band receives light of the green wavelength band. Hereinafter, the pixel $P_{ij}$ that receives light of the green wavelength band is referred to as a G pixel. Similarly, a pixel that receives light of a blue wavelength band is referred to as a B pixel, and a pixel that receives light of a red wavelength band as an R pixel.

Herein, the filter unit U1 passes light of a blue (B) wavelength band $H_B$, a green (G) wavelength band $H_G$, and a red (R) wavelength band $H_R$. In addition, the filter unit U1 is configured using a blue filter (B filter) that passes light of the wavelength band $H_B$, green filters (G filters) that pass light of the wavelength band $H_G$, and a red filter (R filter) that passes light of the wavelength band $H_R$, and forms a so-called Bayer array in which two G filters are diagonally arranged, and the B filter and the R filter are diagonally arranged. In the filter unit U1, density of the G filter is higher than each density of the B filter and the R filter. In other words, the density of the G pixel is higher than each density of the B pixel and the R pixel in the image sensor 202. For example, the blue, green, and red wavelength bands $H_B$, $H_G$, and $H_R$ are given such that, for example, the wavelength band $H_B$ is 380 nm to 500 nm, the wavelength band $H_G$ is 480 nm to 600 nm, and the wavelength band $H_R$ is 580 nm to 650 nm.

Returning to the description of FIGS. 1 and 2, the light guide 203 is configured using a glass fiber or the like and forms a light guide path of light emitted from the light source unit 3.

The illumination lens 204 is provided at a distal end of the light guide 203, diffuses light guided by the light guide 203, and emits the light to the outside of the distal end portion 24.

The A/D converter 205 performs A/D conversion on the electric signal generated by the image sensor 202 and outputs this converted electric signal to the processor 4. The A/D converter 205 converts the electric signal generated by the image sensor 202 into 12-bit digital data (image signal), for example.

The imaging information storage unit 206 stores various programs configured to operate the endoscope 2 and data including various parameters necessary for operations of the endoscope 2, identification information of the endoscope 2, and the like. In addition, the imaging information storage unit 206 includes an identification information storage unit 261 that stores the identification information. The identification information includes unique information (ID) of the endoscope 2, a model year, specification information, a transmission method, filter array information relating to the color filter 202a, and the like. The imaging information storage unit 206 is implemented using a flash memory or the like.

Next, a configuration of the light source unit 3 will be described. The light source unit 3 includes an illumination unit 31 and an illumination controller 32.

The illumination unit 31 switches and emits a plurality of beams of illumination light whose wavelength bands are different from each other under control of the illumination controller 32. The illumination unit 31 includes a light source 31a, a light source driver 31b, a switching filter 31c, a driving unit 31d, a driver 31e, and a condenser lens 31f.

The light source 31a emits white illumination light including light of red, green, and blue wavelength bands $H_R$, $H_G$, and $H_B$ under the control of the illumination controller 32. The white illumination light generated by the light source 31a passes through the switching filter 31c, the condenser lens 31f, and the light guide 203, and then, is emitted to the outside from the distal end portion 24. The light source 31a is implemented using a light source, such as a white LED and a xenon lamp that emits white light.

The light source driver 31b causes the light source 31a to emit the white illumination light by supplying a current to the light source 31a under the control of the illumination controller 32.

The switching filter 31c passes only blue narrow band light and green narrow band light out of the white illumination light emitted by the light source 31a. The switching filter 31c is arranged on an optical path of the white illumination light, emitted from the light source 31a, to be removable under the control of the illumination controller 32. The switching filter 31c is arranged on the optical path of the white illumination light to pass only beams of light having two narrow bands. To be specific, the switching filter 31c passes narrow band illumination light including light of a narrow band $T_B$ (for example, 400 nm to 445 nm) included in the wavelength band $H_B$, and light of a narrow band $T_G$ (for example, 530 nm to 550 nm) included in the wavelength band $H_G$. The narrow bands $T_B$ and $T_G$ are wavelength bands of blue light and green light, respectively, which are easily absorbed by hemoglobin in blood. The narrow band $T_B$ may include at least a wavelength band of 405 nm to 425 nm. The light that is emitted in the state of being limited to such a band is referred to as the narrow band illumination light, and observation of an image using this narrow band illumination light is referred to as narrow band imaging (NBI).

The driving unit 31d is configured using a stepping motor, a DC motor, or the like and causes the switching filter 31c to be inserted into or removed from the optical path of the light source 31a.

The driver 31e supplies a predetermined current to the driving unit 31d under the control of the illumination controller 32.

The condenser lens 31f collects the white illumination light emitted from the light source 31a or the narrow band illumination light that has passed through the switching filter 31c, and emits the collected light to the outside (light guide 203) of the light source unit 3.

The illumination controller 32 controls the light source driver 31b to cause the on/off operation of the light source 31a, and controls the driver 31e to cause the switching filter 31c to be inserted into or removed from the optical path of the light source 31a, thereby controlling types (bands) of the illumination light to be emitted from the illumination unit 31.

To be specific, the illumination controller 32 causes the switching filter 31c to be inserted into or removed from the optical path of the light source 31a so as to control switching of the illumination light emitted from the illumination unit 31 to any light between the white illumination light and the narrow band illumination light. In other words, the illumination controller 32 performs switching between the white light imaging (WLI) using the white illumination light including light of the wavelength bands $H_B$, $H_G$, and $H_R$, and the narrow band imaging (NBI) using the narrow band illumination light including light of the narrow bands $T_B$ and $T_G$.

Here, a green component (the wavelength band $H_G$) becomes a luminance component (first luminance component) in the white light imaging (WLI), and a blue component (the narrow band $T_B$) becomes a luminance component (second luminance component) in the narrow band imaging (NBI). Accordingly, the G pixel corresponds to a first pixel, and the B pixel and the R pixel correspond to second pixels in the image sensor 202 according to the first embodiment.

Figure 5:
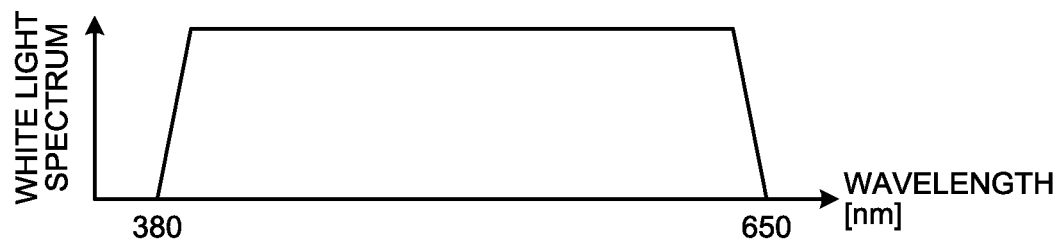
FIG. 5 is a graph illustrating a relationship between a wavelength and the amount of light of illumination light emitted from an illumination unit of the endoscope apparatus according to the first embodiment of the present invention.
Figure 6:
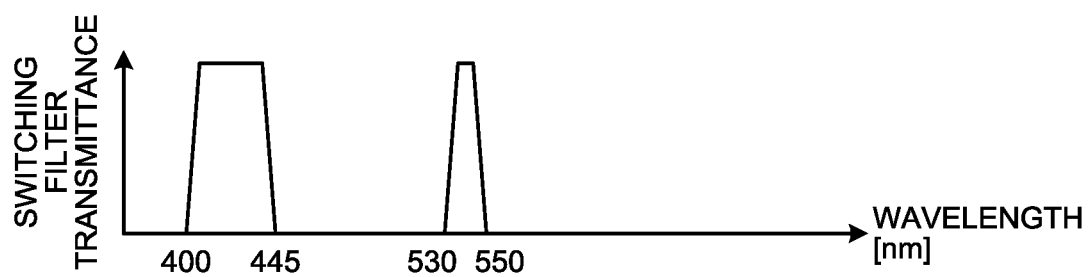
FIG. 6 is a graph illustrating a relationship between a wavelength and transmittance of illumination light from a switching filter included in the illumination unit of the endoscope apparatus according to the first embodiment of the present invention.

FIG. 5 is a graph illustrating a relationship between a wavelength and the amount of light of the illumination light emitted from the illumination unit of the endoscope apparatus according to the first embodiment. FIG. 6 is a graph illustrating a relationship between a wavelength and transmittance of the illumination light from the switching filter included in the illumination unit of the endoscope apparatus according to the first embodiment. When the switching filter 31c is removed from the optical path of the light source 31a under the control of the illumination controller 32, the illumination unit 31 emits the white illumination light including light of the wavelength bands $H_B$, $H_G$ and $H_R$ as in a white light spectrum illustrated in FIG. 5. On the contrary, when the switching filter 31c is inserted into the optical path of the light source 31a under the control of the illumination controller 32, the illumination unit 31 emits the narrow band illumination light including light of the narrow bands $T_B$ and $T_G$ (see FIG. 6).

Next, a configuration of the processor 4 will be described. The processor 4 includes an image processing unit 41, an input unit 42, a storage unit 43, and a control unit 44.

The image processing unit 41 performs predetermined image processing based on the electric signal from the endoscope 2 (A/D converter 205) to generate image information for display of the display unit 5. The image processing unit 41 includes a pre-processing unit 411, an interpolation processing unit 412, and a display image generation processing unit 413.

The pre-processing unit 411 performs optical black (OB) clamp processing, noise reduction (NR) processing, and white balance (WB) processing with respect to the electric signal from the A/D converter 205 to output the signal-processed image signal to the interpolation processing unit 412.

Figure 7:
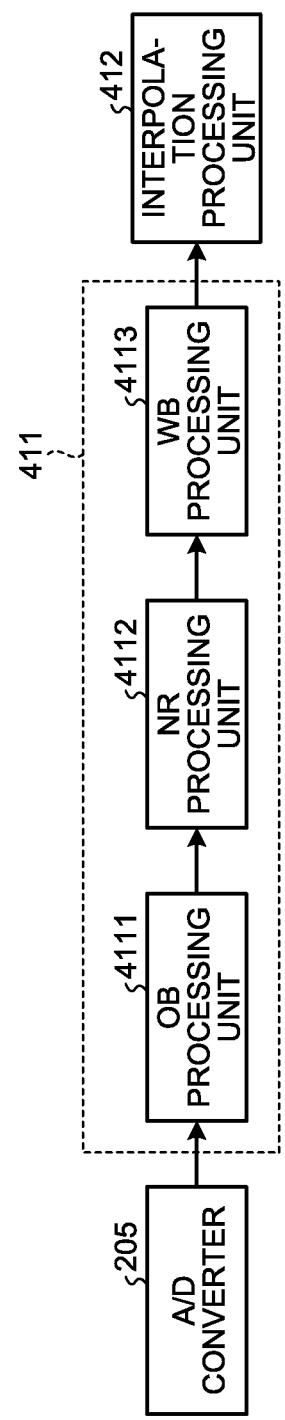
FIG. 7 is a block diagram for describing a configuration of a pre-processing unit according to the first embodiment of the present invention.

FIG. 7 is a block diagram for describing a configuration of the pre-processing unit according to the first embodiment. The pre-processing unit 411 includes an OB processing unit 4111, an NR processing unit 4112, and a WB processing unit 4113.

The OB processing unit 4111 performs the OB clamp processing with respect to each of the R signal, the G signal, and the B signal of the image signal input from the A/D converter 205. In the OB clamp processing, an average value of a predetermined area corresponding to an optical black area is calculated based on the electric signal input from the endoscope 2 (A/D converter 205), and a black level is corrected to a zero value by subtracting the average value from the electric signal.

The NR processing unit 4112 acquires observation method information relating to whether the current observation method is the WLI or the NBI from the control unit 44, and changes the amount of noise reduction according to the observation method information to perform the noise reduction processing on the image signal having been subjected to the OB clamp processing.

The WB processing unit 4113 performs the white balance processing on the image signal having been subjected to the noise reduction processing based on the observation method information, and outputs the image signal after having been subjected to the white balance processing to the interpolation processing unit 412. When two signals (the G signal and the B signal) of channels (color components) are obtained using the narrow band imaging (NBI), the WB processing unit 4113 performs signal balance correction processing between two channels, and performs zero multiplication on the other remaining channel (the R signal in the first embodiment).

The interpolation processing unit 412 generates a color image signal including at least signals of two color components by discriminating an interpolation direction from the correlation of color information (pixel values) of the plurality of pixels based on the image signal input from the pre-processing unit 411 and performing interpolation based on the color information of the pixels arrayed in the discriminated interpolation direction. The interpolation processing unit 412 includes a G-interpolated color difference calculation unit 412a (interpolated color difference calculation unit), a color difference interpolation unit 412b, and a color image signal generation unit 412c (image signal generation unit).

The G-interpolated color difference calculation unit 412a generates a G signal (hereinafter, referred to as an interpolated G signal) that has been interpolated based on a surrounding pixel at the pixel (the R pixel or the B pixel) where the G signal is missed, with respect to the image signal input from the pre-processing unit 411, and outputs a G signal image having the G signal or the interpolated G signal at the entire pixel position. That is, an image signal forming a single image having the pixel value or the interpolated value of the G component at the respective pixels is generated by the interpolation processing of the G-interpolated color difference calculation unit 412a.

In addition, the G-interpolated color difference calculation unit 412a generates an R-G signal or a B-G signal as a color difference signal obtained based on a color difference between the signal of each color component and the interpolated G signal according to a position of the R pixel or the B pixel, and outputs the generated signal as a color difference image signal. The G-interpolated color difference calculation unit 412a outputs the generated G signal image to the color image signal generation unit 412c, and outputs the color difference image signal to the color difference interpolation unit 412b.

The color difference interpolation unit 412b interpolates a missing color difference signal at each pixel position with respect to the color difference image signal input from the G-interpolated color difference calculation unit 412a, and outputs a color difference image signal having the color difference signal at the entire pixel position to the color image signal generation unit 412c. That is, an image signal forming a single image having the value of the color difference signal R-G or B-G at the respective pixels by the interpolation processing of the color difference interpolation unit 412b.

The color image signal generation unit 412c generates an RGB signal or a GB signal by adding the G signal or the interpolated G signal and the color difference signal (the B-G signal or the R-G signal) at each pixel position, and outputs the generated signal to the display image generation processing unit 413 as the color image signal. To be specific, when the observation method is the WLI, the color image signal generation unit 412c acquires the color difference image signal including the B-G signal and the color difference image signal including the R-G signal from the color difference interpolation unit 412b, and generates the signal (RGB signal) including the R component, a G component, and the B component. On the other hand, when the observation method is the NBI, the color image signal generation unit 412c acquires only the color difference image signal including the B-G signal from a B-G interpolation unit 4124 since there is no light having the R component, and generates the signal (GB signal) including the G component and the B component.

The display image generation processing unit 413 executes gradation conversion, magnification processing, structure enhancement processing for structures such as capillaries of a mucosal superficial portion and mucosal fine patterns, and the like with respect to the color image signal generated by the color image signal generation unit 412c. After executing the predetermined processing, the display image generation processing unit 413 outputs the processed signal to the display unit 5 as a display image signal for display.

The input unit 42 is an interface configured to perform input or the like from a user with respect to the processor 4, and includes a power switch configured to turn on or off a power supply, a mode switching button configured to switch a shooting mode and other various modes, an illumination light switching button configured to switch the illumination light of the light source unit 3, and the like.

The storage unit 43 records data including various programs to operate the endoscope apparatus 1 and various parameters necessary for the operation of the endoscope apparatus 1, data necessary for image processing, such as a white balance coefficient depending on the observation method, a program to execute the image processing according to the present invention, and the like. In addition, the storage unit 43 may store information relating to the endoscope 2, for example, a relationship table between the unique information (ID) of the endoscope 2 and information relating to filter arrangement of the color filter 202a. The storage unit 43 is implemented using a semiconductor memory such as a flash memory and a dynamic random access memory (DRAM).

The control unit 44 is configured using a CPU and the like, and performs driving control of the respective elements including the endoscope 2 and the light source unit 3 and input and output control of information with respect to the respective elements, and the like. The control unit 44 transmits setting data (for example, pixels to be read and the like) for imaging control, recorded in the storage unit 43, a timing signal relating to imaging timing, and the like to the endoscope 2 via a predetermined signal line. The control unit 44 outputs color filter information (identification information) acquired via the imaging information storage unit 206 to the image processing unit 41, and outputs information on an insertion or removal operation (arrangement) of the switching filter 31c to the light source unit 3.

Next, the display unit 5 will be described. The display unit 5 receives the display image signal generated by the processor 4 via a video cable, and displays an in-vivo image corresponding to the display image signal. The display unit 5 is configured using liquid crystal or organic electro luminescence (EL).

Figure 8:
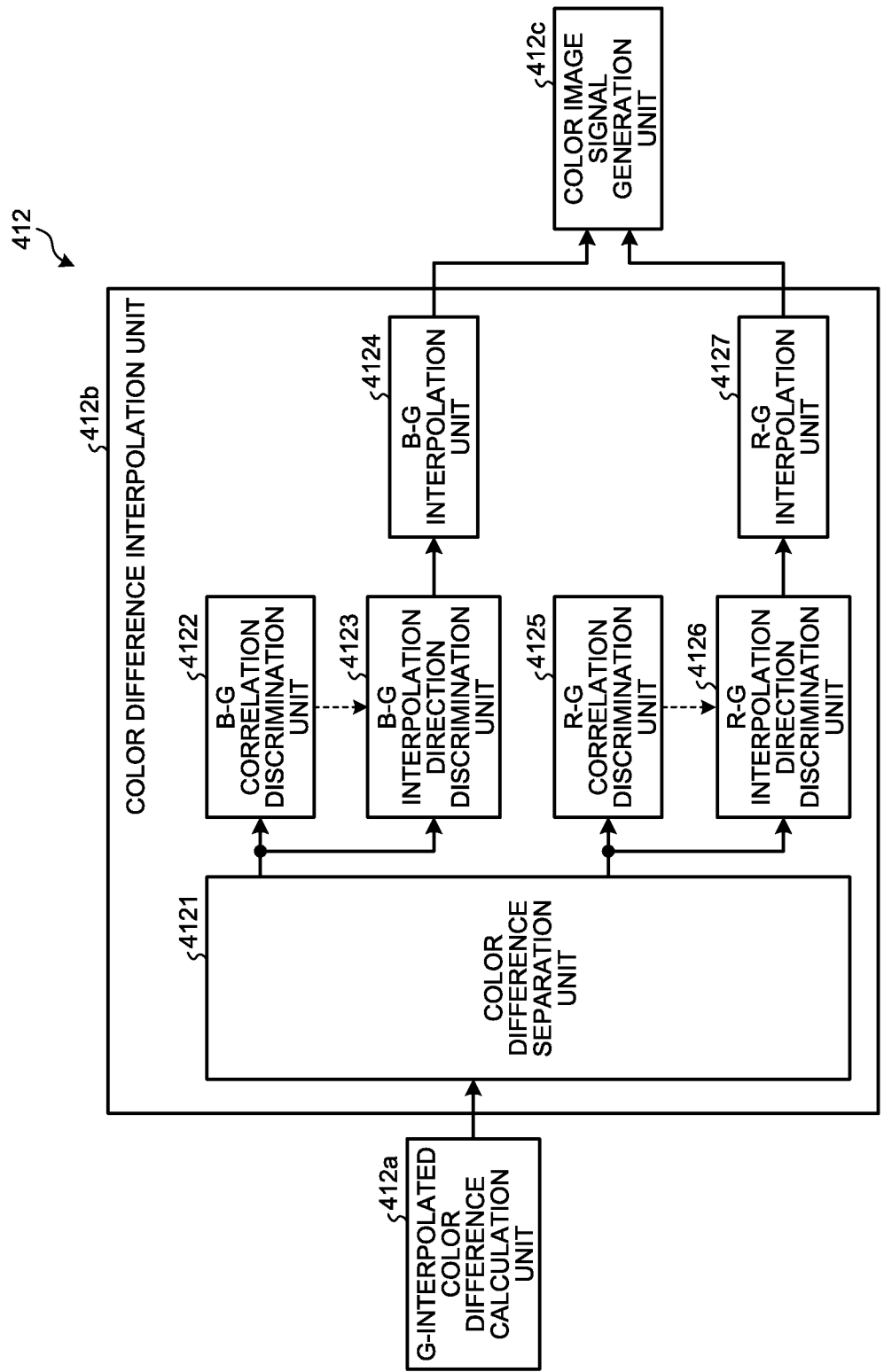
FIG. 8 is a block diagram for describing a configuration of an interpolation processing unit according to the first embodiment of the present invention.

Next, a configuration of the color difference interpolation unit 412b of the interpolation processing unit 412 will be described with reference to the drawings. FIG. 8 is a block diagram for describing a configuration of the interpolation processing unit according to the first embodiment. The color difference interpolation unit 412b includes a color difference separation unit 4121, a B-G correlation discrimination unit 4122, a B-G interpolation direction discrimination unit 4123, a B-G interpolation unit 4124, an R-G correlation discrimination unit 4125, an R-G interpolation direction discrimination unit 4126, and an R-G interpolation unit 4127.

The color difference separation unit 4121 separates the color difference image signal output from the G-interpolated color difference calculation unit 412a into the B-G signal and the R-G signal, and outputs the B-G signal to the B-G correlation discrimination unit 4122 and the B-G interpolation direction discrimination unit 4123 and outputs the R-G signal to the R-G correlation discrimination unit 4125 and the R-G interpolation direction discrimination unit 4126.

FIG. 9 is a schematic diagram for describing demosaicing processing performed by the processor according to the first embodiment. The separated B-G signal and R-G signal are arranged to correspond to the B pixel position and the R pixel position, respectively, as in the schematic diagram illustrated in FIG. 9.

The B-G correlation discrimination unit 4122 sets the R pixel having the R-G signal as a pixel of interest with respect to the B-G signal output from the color difference separation unit 4121, and calculates a correlation of the B-G signal at a pixel adjacent to the pixel of interest. FIG. 10 is a schematic diagram for describing the demosaicing processing performed by the processor according to the first embodiment. To be specific, the B-G correlation discrimination unit 4122 sets a coordinate of the pixel (pixel $P_{ij}$) of interest as (k,l), and calculates a correlation value Ss in an obliquely upward direction based on the following Formula (1) when color difference signal values of the B-G signals at four adjacent pixel positions are set as B-G (k−1,l−1), B-G (k+1,l−1), B-G (k−1,l+1), and B-G (k+1,l+1) as illustrated in FIG. 10. Hereinafter, the obliquely upward direction indicates a direction to the upper right from the lower left in the pixel arrangement illustrated in FIG. 3, and the obliquely downward direction indicates a direction to the lower right from the upper left in the pixel arrangement illustrated in FIG. 3. In addition, when a pixel has no adjacent pixel, such as a pixel positioned at an outer edge, a signal value of a pixel positioned at, for example, a folded position is used.

$$Ss=|B\text{-}G(k-1,l+1)-B\text{-}G(k+1,l-1)| \quad (1)$$

In addition, the B-G correlation discrimination unit 4122 calculates a correlation value Sb in the obliquely downward direction based on the following Formula (2).

$$Sb=|B\text{-}G(k-1,l-1)-B\text{-}G(k+1,l+1)| \quad (2)$$

Although the calculation is performed using signal values of two pixels positioned in the oblique direction in the above-described Formulas (1) and (2), the invention is not limited thereto. It is possible to improve the reliability of the correlation value calculated using the B-G signals at the pixels which are separated in the same direction around the pixel of interest.

When an absolute value |Ss−Sb| of a difference between the correlation values Ss and Sb is larger than a threshold designated in advance, the B-G correlation discrimination unit 4122 determines a direction of the correlation value, which is a smaller value between the correlation values Ss and Sb, as a direction with the higher correlation. On the contrary, when the difference absolute value |Ss−Sb| is smaller than the threshold, the B-G correlation discrimination unit 4122 determines that there is no correlation in a specific direction. The B-G correlation discrimination unit 4122 outputs determination information, which indicates any of "the obliquely upward direction", "the obliquely downward direction" and "no correlation in a specific direction", to the B-G interpolation direction discrimination unit 4123. The threshold is set as a value obtained in view of noise included in the signal.

The B-G interpolation direction discrimination unit 4123 calculates an interpolated color difference signal value B-G (k,l) of the B-G signal at the pixel (k,l) of interest based on any formula among the following Formulas (3) to (5) using the determination information from the B-G correlation discrimination unit 4122 and the color difference signal value of the B-G signal.

Determination Information is "Obliquely Upward Direction"

In a case where the determination information is "the obliquely upward direction", the B-G interpolation direction discrimination unit 4123 calculates the interpolated color difference signal value B-G (k,l) of the B-G signal at the pixel (k,l) of interest based on the following Formula (3).

$$B\text{-}G(k,l)=\{B\text{-}G(k-1,l+1)+B\text{-}G(k+1,l-1)\}/2 \quad (3)$$

Determination Information is "Obliquely Downward Direction"

In a case where the determination information is "the obliquely downward direction", the B-G interpolation direction discrimination unit 4123 calculates the interpolated color difference signal value B-G (k,l) of the B-G signal at the pixel (k,l) of interest based on the following Formula (4).

$$B\text{-}G(k,l)=\{B\text{-}G(k-1,l-1)+B\text{-}G(k+1,l+1)\}/2 \quad (4)$$

Determination Information is "No Correlation in Specific Direction"

In a case where the determination information is "no correlation in a specific direction", the B-G interpolation direction discrimination unit 4123 calculates the interpolated color difference signal value B-G (k,l) of the B-G signal at the pixel (k,l) of interest based on the following Formula (5).

$$B-G(k,l) = \{B-G(k-1,l+1) + B-G(k+1,l-1) + B-G(k-1,l-1) + B-G(k+1,l+1)\}/4 \quad (5)$$

Although the interpolation is performed using an average value of the B-G signals of four surrounding pixels in the above-described Formula (5), the interpolation may be performed using the B-G signals of sixteen surrounding pixels or more with which a high spatial frequency can be maintained.

The B-G interpolation direction discrimination unit 4123 outputs a color difference signal relating to a color difference B-G in which the B-G signals including the interpolated color difference signal, obtained by calculation of the interpolated color difference signal value B-G (k,l) with respect to the pixel (k,l) of interest, are arranged in a checkerboard pattern to the B-G interpolation unit 4124.

The B-G interpolation unit 4124 calculates the interpolated color difference signal value of the B-G signal at a pixel position where a color difference signal is missed with respect to the color difference signal (B-G signal) from the B-G interpolation direction discrimination unit 4123. The B-G interpolation unit 4124 calculates an interpolated value B-G (k,l−1) at a pixel position (k,l−1) where the color difference signal is missed in the pixel arrangement illustrated in FIG. 10, for example, based on the following Formula (6).

$$B - G(k, l-1) = \{B - G(k-1, l-1) + B - G(k, l-2) + B - G(k+1, l-1) + B - G(k, l)\}/4 \quad (6)$$

Although the interpolation is performed using an average value of the B-G signals of four surrounding pixels in the above-described Formula (6), the interpolation may be performed using the B-G signals of sixteen surrounding pixels or more with which a high spatial frequency can be maintained.

The B-G interpolation unit 4124 outputs a color difference image signal having the B-G signal at the entire pixel position, obtained by calculation of the interpolated color difference signal value at the pixel position where the B-G signal is missed to the color image signal generation unit 412c. That is, a color difference signal forming a single image having the color difference signal value or the interpolated color difference signal value relating to the color difference signal B-G at the respective pixels by the interpolation processing of the B-G interpolation unit 4124.

The R-G correlation discrimination unit 4125 sets the B pixel having the B-G signal as a pixel of interest with respect to the R-G signal output from the color difference separation unit 4121, and calculates a correlation of the R-G signal at a pixel adjacent to the pixel of interest, similarly to the B-G correlation discrimination unit 4122. The R-G correlation discrimination unit 4125 calculates the correlation values Ss and Sb by replacing B with R in Formulas (1) and (2). The R-G correlation discrimination unit 4125 determines any of "the obliquely upward direction", "the obliquely downward direction", and "no correlation in a specific direction" based on the correlation value Ss, the correlation value Sb, the difference absolute value |Ss−Sb|, and the threshold, and outputs determination information indicating a result of the determination to the R-G interpolation direction discrimination unit 4126.

The R-G interpolation direction discrimination unit 4126 calculates an interpolated color difference signal value R-G (k,l) of the R-G signal at the pixel (k,l) of interest based on any formula among the above Formulas (3) to (5) using the determination information from the R-G correlation discrimination unit 4125 and the color difference signal value of the R-G signal, similarly to the B-G interpolation direction discrimination unit 4123. The R-G interpolation direction discrimination unit 4126 calculates the interpolated color difference signal value R-G (k,l) by replacing B with R in Formulas (3) to (5). The R-G interpolation direction discrimination unit 4126 outputs a color difference signal relating to a color difference R-G in which the R-G signals including the interpolated color difference signal, obtained by calculation of the interpolated color difference signal value R-G (k,l) with respect to the pixel (k,l) of interest, are arranged in a checkerboard pattern to the R-G interpolation unit 4127.

The R-G interpolation unit 4127 calculates the interpolated color difference signal value of the R-G signal at a pixel position where a color difference signal is missed with respect to the color difference signal (R-G signal) from the R-G interpolation direction discrimination unit 4126, similarly to the B-G interpolation unit 4124. The R-G interpolation unit 4127 outputs a color difference image signal having the R-G signal at the entire pixel position, obtained by calculation of the interpolated color difference signal value at the pixel position where the R-G signal is missed to the color image signal generation unit 412c. That is, a color difference signal forming a single image having the color difference signal value or the interpolated color difference signal value relating to the color difference signal R-G at the respective pixels by the interpolation processing of the R-G interpolation unit 4127.

The color difference interpolation unit 412b outputs the color difference signal, obtained by the above-described interpolation processing, to the color image signal generation unit 412c. Here, the color difference image signal including the B-G signal and the color difference image signal including the R-G signal are output from the B-G interpolation unit 4124 and the R-G interpolation unit 4127, respectively, when the observation method is the WLI. On the other hand, when the observation method is the NBI, only the color difference image signal including the B-G signal from the B-G interpolation unit 4124 is input to the color image signal generation unit 412c since there is no light having the R component.

Figure 11:
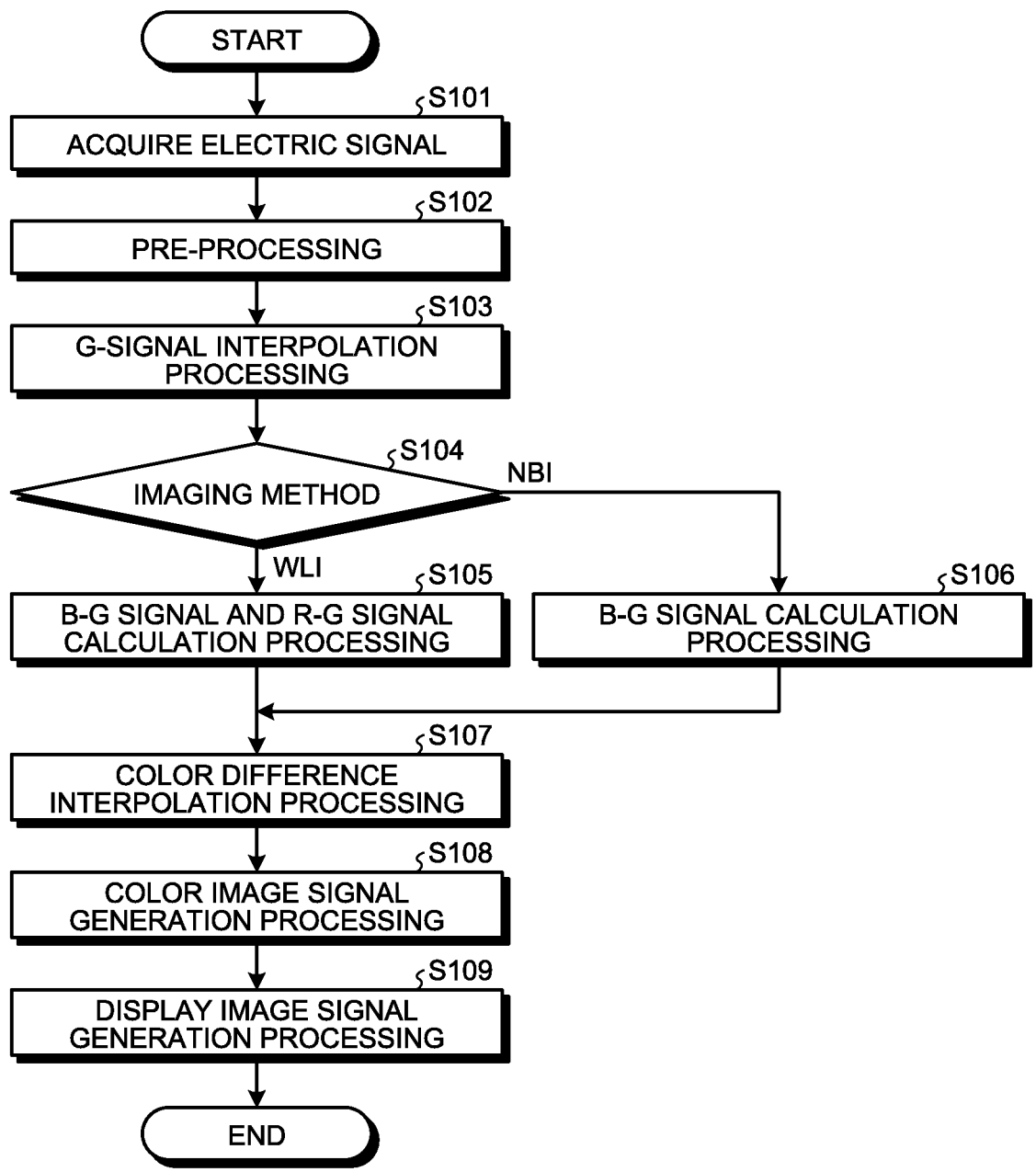
FIG. 11 is a flowchart for describing signal processing which is performed by a processor according to the first embodiment of the present invention.

Next, the signal processing (an image processing method) performed by the processor 4 will be described with reference to the drawings. FIG. 11 is a flowchart for describing signal processing which is performed by the processor according to the first embodiment. When acquiring an electric signal from the endoscope 2 (distal end portion 24), the processor 4 outputs the electric signal to the pre-processing unit 411 (step S101). The electric signal from the endoscope 2 is a signal that is generated by the image sensor 202 and includes RAW image data that has been converted into a digital signal by the A/D converter 205.

When the electric signal is input to the pre-processing unit 411, the pre-processing unit 411 performs the OB clamp processing, the noise reduction processing, and the white balance processing, described above, and outputs the signal-processed image signal to the interpolation processing unit 412 (step S102).

When the electric signal having been subjected to the signal processing by the pre-processing unit 411 is input to the interpolation processing unit 412, the G-interpolated color difference calculation unit 412a generates the interpolated G signal at the pixel (the R pixel or the B pixel) where the G signal is missed, and outputs the G signal image having the G signal (pixel value) or the interpolated G signal (interpolated value) at all of the pixel positions, to the color image signal generation unit 412c (step S103).

Thereafter, the G-interpolated color difference calculation unit 412a determines which of the white light imaging and the narrow band imaging is used to generate the input electric signal (step S104). To be specific, the G-interpolated color difference calculation unit 412a determines which of the imaging methods is used to generate the input electric signal based on a control signal (for example, information on the illumination light or information indicating the imaging method) from the control unit 44, for example.

If the input electric signal is generated using the white light imaging (step S104; WLI), the G-interpolated color difference calculation unit 412a generates the R-G signal and the B-G signal, which are the color difference signals obtained based on the color difference between the signal of each color component and the interpolated G signal according to positions of the R pixel and the B pixel, and outputs the generated signals to the color difference interpolation unit 412b as the color difference image signals (step S105).

On the other hand, if the input electric signal is generated using the narrow band imaging (step S104; NBI), the G-interpolated color difference calculation unit 412a generates the B-G signal, which is the color difference signals obtained based on the color difference between the signal of the B component and the interpolated G signal according to the B pixel position, and outputs the generated signal to the color difference interpolation unit 412b as the color difference image signal (step S106). The processing of steps S103 to S106 corresponds to an interpolated color difference calculation step (interpolated color difference calculation process) according to the present invention.

The color difference interpolation unit 412b performs color difference interpolation processing based on the color difference image signal acquired by the G-interpolated color difference calculation unit 412a (step S107). To be specific, the color difference interpolation unit 412b interpolates a missing color difference signal at each pixel position with respect to the color difference image signal input from the G-interpolated color difference calculation unit 412a, and outputs the color difference image signal having the color difference signal at the entire pixel position to the color image signal generation unit 412c. That is, through the interpolation processing of the color difference interpolation unit 412b, the image signal forming the single image, which has the values of the color difference signals R-G and B-G at the respective pixels, is generated in the white light imaging, and the image signal forming the single image, which has the value of the color difference signal B-G at the respective pixels, is generated in the narrow band imaging. The processing of step S107 corresponds to a color difference interpolation step (color difference interpolation process) according to the present invention.

The color image signal generation unit 412c generates a color image signal forming a color image using the pixel value and the interpolated value of the G component generated by the G-interpolated color difference calculation unit 412a, and a signal value of the color difference image signal generated by the color difference interpolation unit 412b (step S108). To be specific, the color image signal generation unit 412c generates an RGB signal or a GB signal by adding the G signal or the interpolated G signal and the color difference signal (the B-G signal or the R-G signal) at each pixel position, and outputs the generated signal to the display image generation processing unit 413 as the color image signal. The processing of step S108 corresponds to an image signal generation step (image signal generation process) according to the present invention.

The display image generation processing unit 413 executes the gradation conversion, magnification processing, the structure enhancement processing for the structures such as the capillaries of the mucosal superficial portion and the mucosal fine patterns, and the like with respect to the color image signal generated by the color image signal generation unit 412c, to generate the display image signal for display (step S109). After executing the predetermined processing, the display image generation processing unit 413 outputs the processed signal to the display unit 5 as the display image signal.

According to the above-described first embodiment, the endoscope apparatus capable of switching between the WLI and the NBI is configured to determine a higher-correlation direction using only the surrounding B-G signal of the position of the pixel of interest with respect to the B-G signal and to perform the interpolation using the B-G signal in the determined higher-correlation direction. Thus, it is possible to perform the interpolation also relating to the capillaries of the mucosal superficial portion, blood vessels in a mucosal middle layer, and blood vessels in a mucosal deep layer in a direction along a blood vessel travel route, and particularly, to maintain resolving power of the B-G signal in the NBI. If it is possible to maintain the resolving power of the B-G signal, it is also possible to maintain resolving power of the B signal that is calculated by adding the G signal to the B-G signal using the color image signal generation unit 412c. That is, it is possible to maintain the resolving power of the B signal, which enables visualization of the capillaries of the mucosal superficial portion, by the above-described interpolation processing. According to the first embodiment, the image signal generation processing is performed based on the electric signal generated using the Bayer array where the density of the G pixels is high in the WLI, and thus, it is possible to obtain a high-resolution image in any of the white light imaging and the narrow band imaging.

Modified Example of First Embodiment

Figure 12:
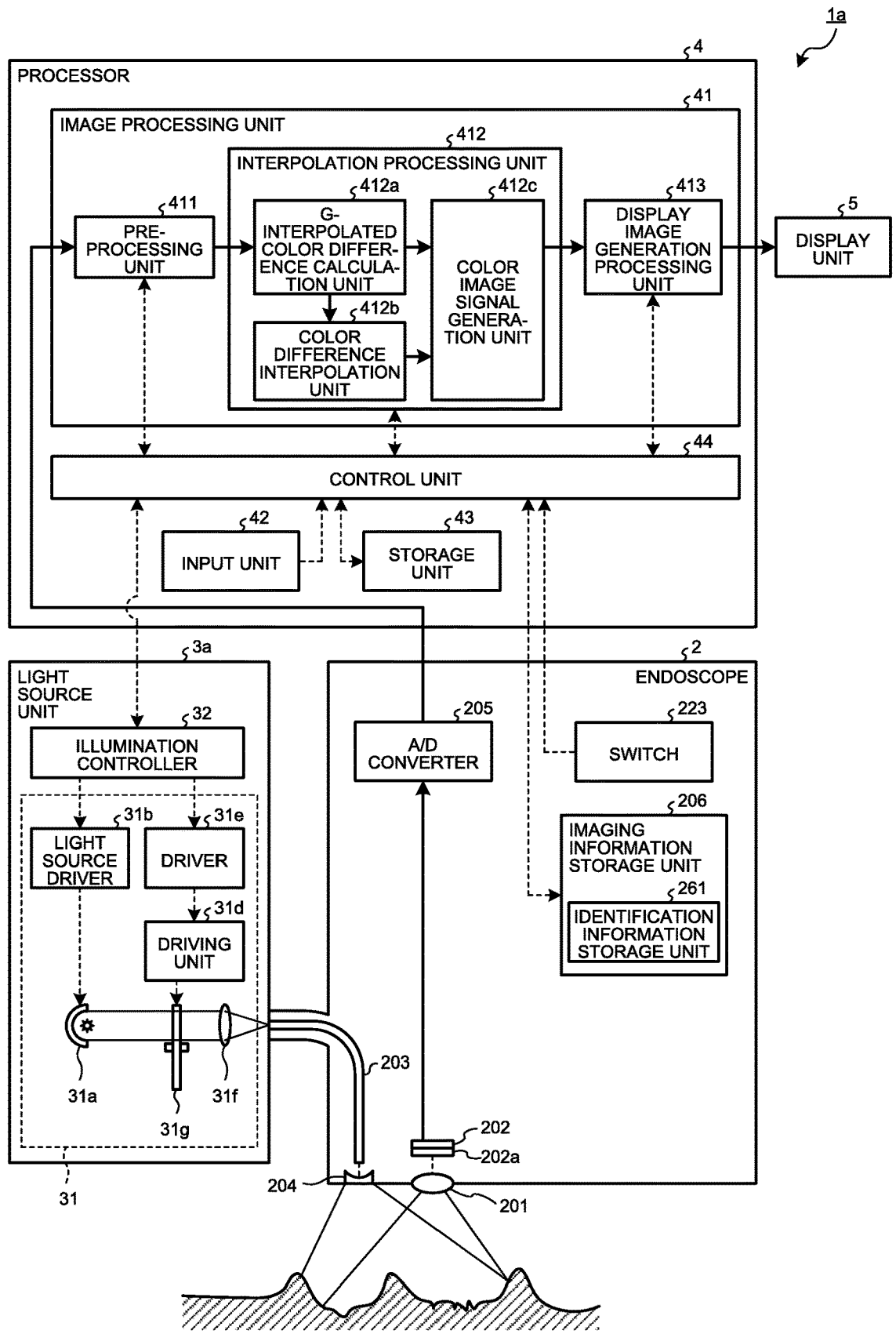
FIG. 12 is a schematic diagram illustrating a schematic configuration of an endoscope apparatus according to a modified example of the first embodiment of the present invention.

FIG. 12 is a schematic diagram illustrating a schematic configuration of an endoscope apparatus according to a modified example of the first embodiment of the present invention. In the first embodiment, the light source unit 3 includes the switching filter 31c, and the switching between the white light imaging and the narrow band imaging using the narrow band illumination light having light of the narrow bands $T_B$ and $T_G$ is performed by the insertion or removal of the switching filter 31c. In this modified example, however, a light source unit 3a is provided instead of the light source unit 3, and the imaging method is switched by a rotation filter 31g.

The endoscope apparatus 1a according to the present modified example includes the endoscope 2, the processor 4, and the display unit 5, which are described above, and the light source unit 3a that generates illumination light emitted from a distal end of the endoscope 2. The light source unit 3a includes the illumination unit 31 and the illumination controller 32. The illumination unit 31 switches and emits a plurality of beams of illumination light whose wavelength bands are different from each other under control of the illumination controller 32. The illumination unit 31 includes the light source 31a, the light source driver 31b, the driving unit 31d, the driver 31e, and the condenser lens 31f, which are described above, and the rotation filter 31g.

Figure 13:
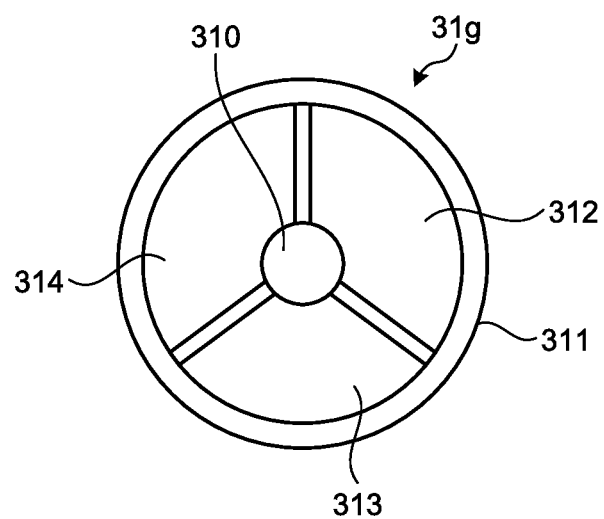
FIG. 13 is a schematic diagram illustrating a configuration of a rotation filter of a light source unit according to the modified example of the first embodiment of the present invention.

FIG. 13 is a schematic diagram illustrating a configuration of the rotation filter of the light source unit according to the modified example of the first embodiment of the present invention. The rotation filter 31g includes a rotation shaft 310 and a discoid rotation unit 311 which is supported by the rotation shaft 310. The rotation unit 311 includes three filters (filters 312 to 314) which are arranged, respectively, in three areas obtained by dividing a main surface.

The filter 312 passes the white illumination light including light of red, green, and blue wavelength bands $H_R$, $H_G$, and $H_B$.

The filter 313 passes narrow band illumination light (referred to as first narrow band illumination light in the present modified example) including light of the narrow band $T_B$ (for example, 400 nm to 445 nm) included in the wavelength band $H_B$, and light of the narrow band $T_G$ (for example, 530 nm to 550 nm) included in the wavelength band $H_G$. The light that is caused to pass through the filter 313 corresponds to the narrow band illumination light in the above-described narrow band imaging (NBI).

Figure 14:
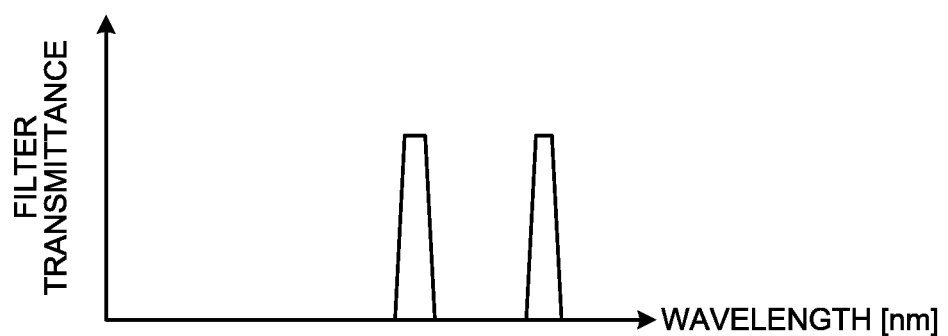
FIG. 14 is a graph illustrating a relationship between a wavelength and transmittance of illumination light according to a filter included in the illumination unit of the endoscope apparatus according to the modified example of the first embodiment of the present invention.

FIG. 14 is a graph illustrating a relationship between a wavelength and transmittance of illumination light according to the filter included in the illumination unit of the endoscope apparatus according to the modified example of the first embodiment of the present invention. The filter 314 passes narrow band illumination light (referred to as second narrow band illumination light in the present modified example) including light of the narrow band $T_R$ included in the wavelength band $H_R$, and light of the narrow band $T_G$ included in the wavelength band $H_G$. The light of the narrow band $T_G$ that is caused to pass through the filter 314 may be the same light of the narrow band $T_G$ in the above-described narrow band imaging (NBI) or may be light of a different band. In the second narrow band illumination light, for example, a color component which changes greatly is selected as a luminance component between the red color component (the narrow band $T_R$) and the green component (the narrow band $T_G$).

The illumination controller 32 controls the light source driver 31b to cause the on/off operation of the light source 31a, and controls the driver 31e to arrange any filter of the filters 312 to 314 by rotating the rotation filter 31g (rotation shaft 310) on the optical path of the light source 31a, thereby controlling types (bands) of the illumination light to be emitted from the illumination unit 31.

Even in the present modified example, the image processing unit 41 executes the signal processing to generate the display image signal. There is no light of the B component in the case of observation using the second narrow band illumination light, and thus, only the color difference image signal including the R-G signal is input to the color image signal generation unit 412c from the R-G interpolation unit 4127, and the signal (RG signal) including the R component and the G component is generated by the color image signal generation unit 412c.

Second Embodiment

Figure 15:
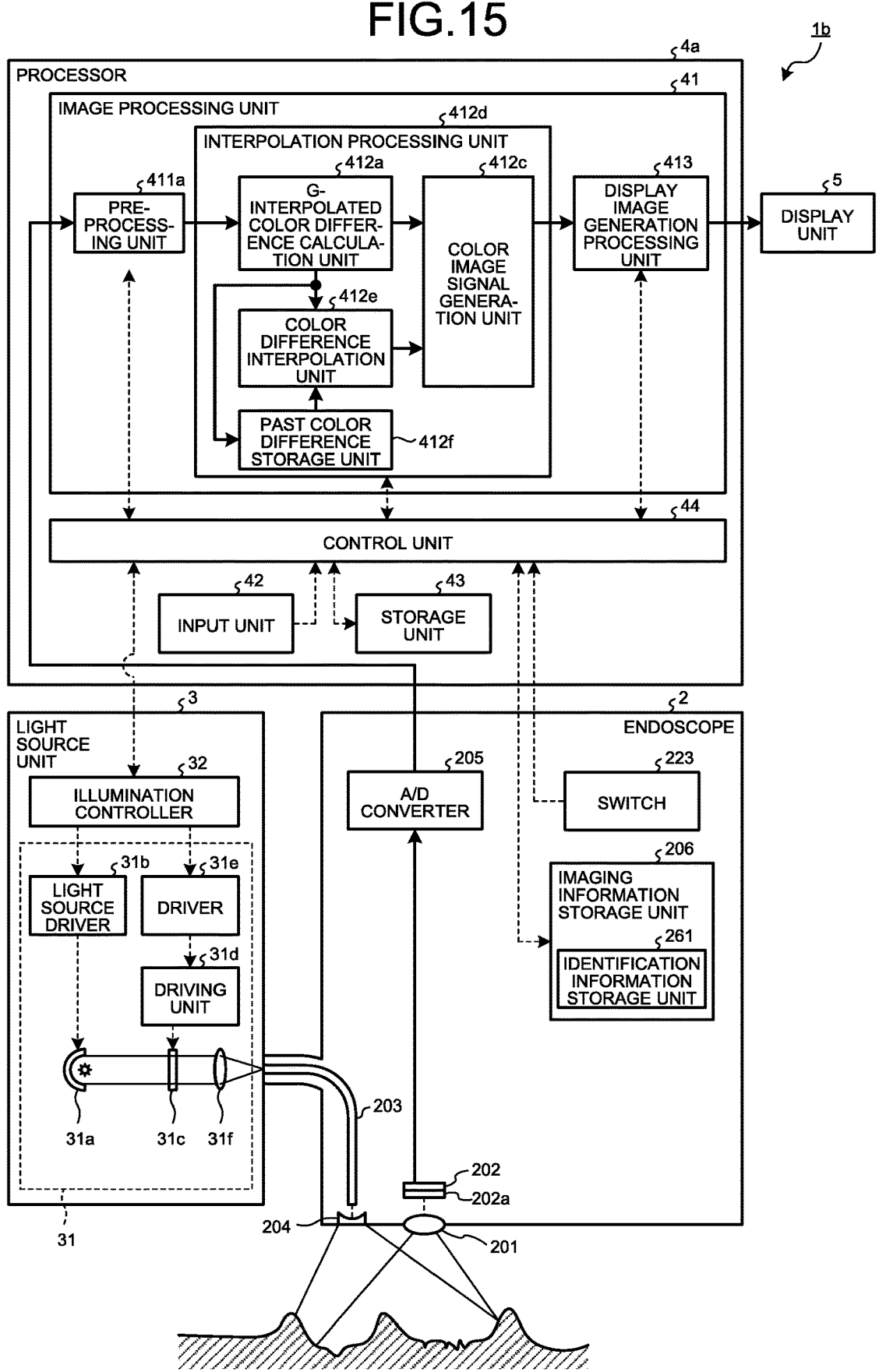
FIG. 15 is a schematic diagram illustrating a schematic configuration of an endoscope apparatus according to a second embodiment of the present invention.

Next, a second embodiment of the present invention will be described. FIG. 15 is a schematic diagram illustrating a schematic configuration of an endoscope apparatus according to the second embodiment. The same elements as those in the first embodiment will be denoted by the same reference signs. Although the case of performing the interpolation processing using a single frame has been described in the above-described first embodiment, interpolation processing is performed using a plurality of frames including the past frame in the second embodiment.

An endoscope apparatus 1b according to the second embodiment includes the endoscope 2, the light source unit 3, and the display unit 5, which are described above, and a processor 4a that executes predetermined image processing on an electric signal acquired by the endoscope 2 and comprehensively controls the entire operation of the endoscope apparatus 1b. The processor 4a includes the image processing unit 41, the input unit 42, the storage unit 43, and the control unit 44.

The image processing unit 41 performs predetermined image processing based on the electric signal from the endoscope 2 (A/D converter 205) to generate image information for display of the display unit 5. The image processing unit 41 includes the above-described display image generation processing unit 413, a pre-processing unit 411a, and an interpolation processing unit 412d.

Similarly to the above-described pre-processing unit 411, the pre-processing unit 411a performs OB clamp processing, noise reduction processing, and white balance processing with respect to the electric signal from the A/D converter 205, and outputs the signal-processed image signal to the interpolation processing unit 412d.

Figure 16:
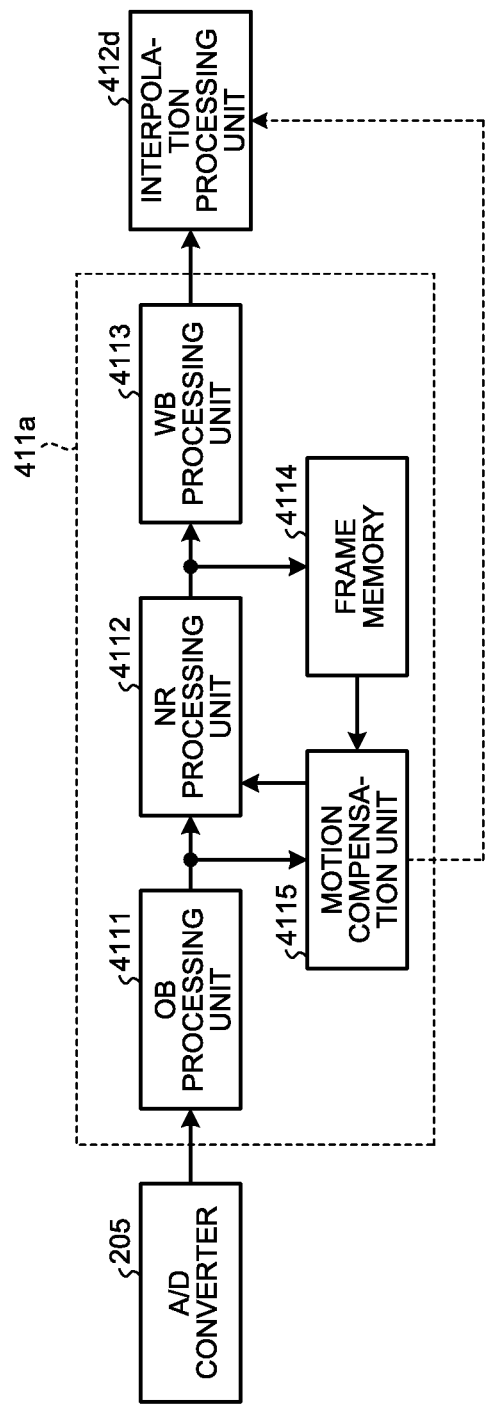
FIG. 16 is a block diagram for describing a configuration of a pre-processing unit according to the second embodiment of the present invention.

FIG. 16 is a block diagram for describing a configuration of the pre-processing unit according to the second embodiment. The pre-processing unit 411a includes the OB processing unit 4111, the NR processing unit 4112, and the WB processing unit 4113, which are described above, and a frame memory 4114, and a motion compensation unit 4115.

The frame memory 4114 stores an image signal corresponding to one frame that has been subjected to the noise reduction processing by the NR processing unit 4112, and outputs the image signal to the motion compensation unit 4115.

The motion compensation unit 4115 detects a motion of an image between first and second motion detection images as a motion vector by a known block matching method using the first motion detection image based on an image signal of the past frame and the second motion detection image based on an image signal of the current frame.

Figure 17:
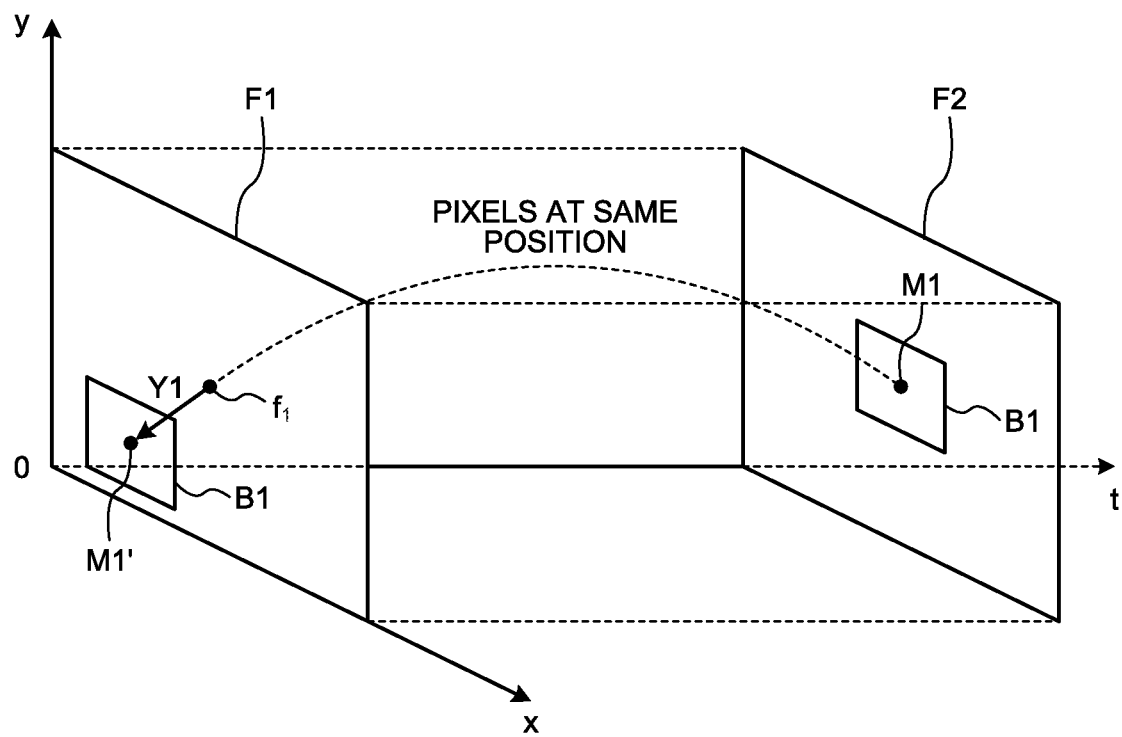
FIG. 17 is a diagram for schematically describing a motion between images obtained at different timings of imaging performed by a motion vector detection processing unit of the endoscope apparatus according to the second embodiment of the present invention.

FIG. 17 is a diagram for schematically describing a motion between images obtained at different timings of imaging performed by a motion vector detection processing unit of the endoscope apparatus according to the second embodiment. The motion compensation unit 4115 adds R signals, G signals (two G signals) and B signals of the filter unit U1 illustrated in FIG. 4, and obtains each average thereof to generate a pseudo luminance signal with respect to a first motion detection image F1 based on the image signal of the past frame (frame immediately before the current frame) at a different time t output from the frame memory 4114, and a second motion detection image F2 based on the image signal of the current frame output from the OB processing unit 4111. The detection is performed by general block matching processing, for example, as a method of detecting the motion. To be specific, the detection is performed on any position in the first motion detection image F1 to which a pixel M1 of the second motion detection image F2 has been moved. The motion compensation unit 4115 uses a block B1 (small area) around the pixel M1 as a template, scans the first motion detection image F1 in the template of the block B1 around a pixel $f_1$ of the first motion detection image F1, which is at the same position as a position of the pixel M1 of the second motion detection image F2, and sets a center pixel, at a position with the smallest sum of absolute differences among the templates, as a pixel M1'. The motion compensation unit 4115 detects a motion amount Y1 from the pixel M1 (pixel $f_1$) to the pixel M1' in the first motion detection image F1 as the motion vector, and performs this process to all pixels as image processing targets. Hereinafter, a coordinate of the pixel M1 is represented by (x,y), and an x component of the motion vector in the coordinate (x,y) is denoted by Vx(x,y) and a y component is denoted by Vy(x,y). An x direction corresponds to a right-and-left (horizontal) direction of pixels illustrated in FIG. 3, and a y direction corresponds to an up-and-down (vertical) direction. In addition, when a coordinate of the pixel M1' in the first motion detection image F1 is represented by (x',y'), x' and y' are defined using the following Formulas (7) and (8), respectively. The motion compensation unit 4115 outputs information on the detected motion vector (including positions of the pixels M1 and M1') to the interpolation processing unit 412d.

$$x'=x+Vx(x,y) \quad (7)$$

$$y'=y+Vy(x,y) \quad (8)$$

In addition, the motion compensation unit 4115 performs positioning between the image signal of the immediately previous frame output from the frame memory 4114 and the image signal of the current frame (positioning between the first motion detection image F1 and the second motion detection image F2) based on the detected motion vector for each pixel, thereby generating a motion-compensated image signal. The generated motion-compensated image signal is output to the NR processing unit 4112.

The NR processing unit 4112 performs weighting and averaging between the image signal of the current frame output from the OB processing unit 4111 and the motion-compensated image signal output from the motion compensation unit 4115 using a predetermined weight for each pixel to reduce noise of the image signal of the current frame, and outputs the noise-reduced image signal to the WB processing unit 4113 and the frame memory 4114. Herein, the amount of the predetermined weight for weighting and addition is determined based on observation method information from the control unit 44.

The interpolation processing unit 412d generates a color image signal including at least signals of two color components by discriminating an interpolation direction from the correlation of color information (pixel values) of the plurality of pixels based on the image signal and the motion vector information input from the pre-processing unit 411a and performing interpolation based on the color information of the pixels arrayed in the discriminated interpolation direction. The interpolation processing unit 412d includes the G-interpolated color difference calculation unit 412a and the color image signal generation unit 412c, which are described above, a color difference interpolation unit 412e, and a past color difference storage unit 412f.

The color difference interpolation unit 412e interpolates a missing color difference signal at each pixel position by referring to the motion vector information, with respect to the color difference image signal input from the G-interpolated color difference calculation unit 412a, and outputs the color difference image signal having the color difference signal at the entire pixel position to the color image signal generation unit 412c. That is, an image signal forming a single image having the value of the color difference signal R-G or B-G at the respective pixels by the interpolation processing of the color difference interpolation unit 412e.

The past color difference storage unit 412f is configured using a plurality of frame memories as ring buffers, and stores the color difference image signal output from the G-interpolated color difference calculation unit 412a in the frame memories. The frame memory to be recorded herein, is a color difference image signal in a period which is at least one frame period before the current frame. It is a matter of course that color difference signal images corresponding to a plurality of frame periods may be stored.

Figure 18:
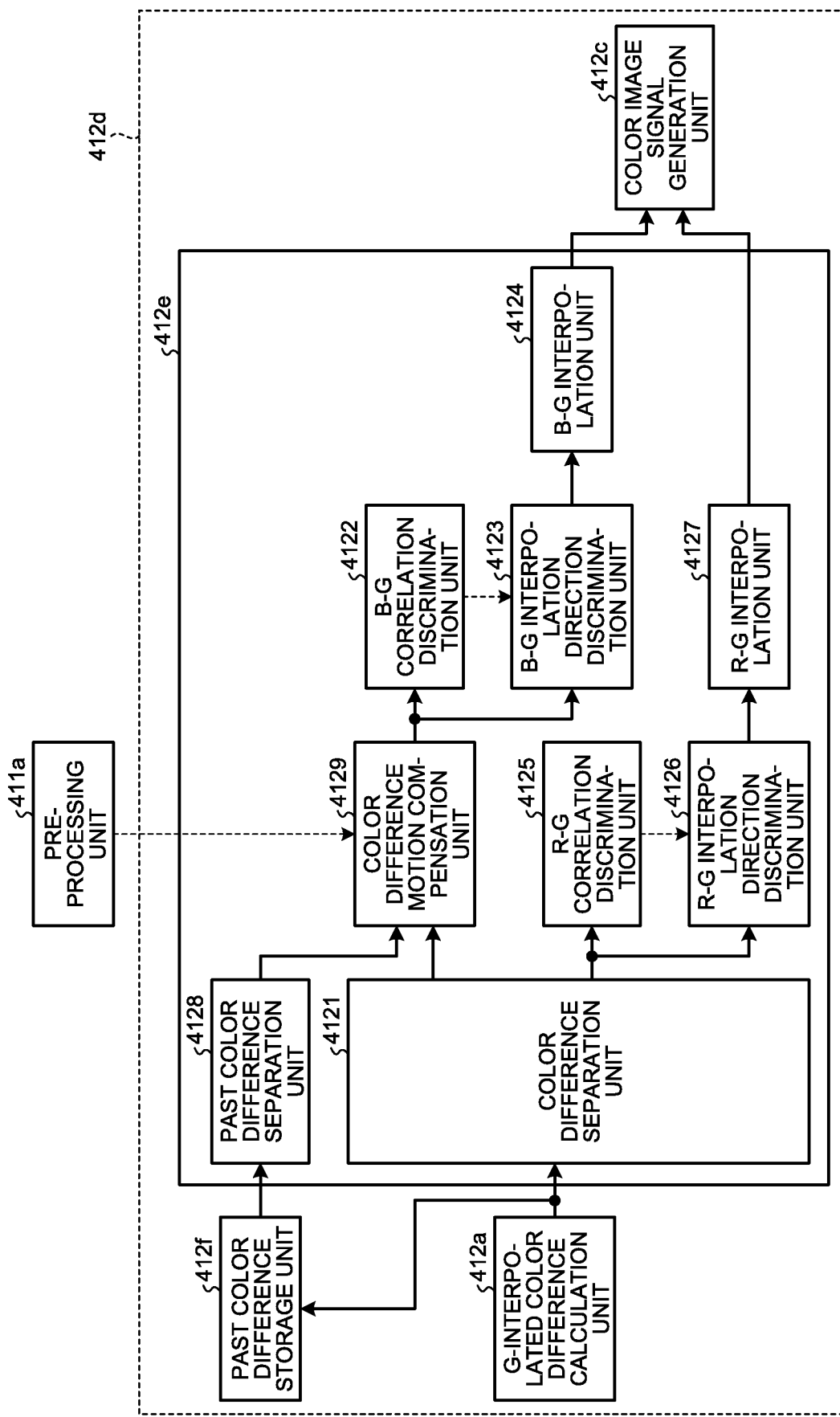
FIG. 18 is a block diagram for describing a configuration of an interpolation processing unit of a processor according to the second embodiment of the present invention.

Next, a configuration of the color difference interpolation unit 412e of the interpolation processing unit 412d will be described with reference to the drawings. FIG. 18 is a block diagram for describing a configuration of the interpolation processing unit of a processor according to the second embodiment. The color difference interpolation unit 412e includes the color difference separation unit 4121, the B-G correlation discrimination unit 4122, the B-G interpolation direction discrimination unit 4123, the B-G interpolation unit 4124, the R-G correlation discrimination unit 4125, the R-G interpolation direction discrimination unit 4126, and the R-G interpolation unit 4127, which are described above, a past color difference separation unit 4128, and a color difference motion compensation unit 4129.

The past color difference separation unit 4128 acquires a color difference image signal of an immediately previous frame with reference to the past color difference storage unit 412f. In the second embodiment, the past color difference separation unit 4128 extracts and outputs only the B-G signal to the color difference motion compensation unit 4129.

The color difference motion compensation unit 4129 corrects the B-G signal based on the motion vector information output from the pre-processing unit 411a, a B-G signal as a color difference signal of the past frame output from the past color difference separation unit 4128, and a B-G signal of the current frame output from the color difference separation unit 4121. The color difference motion compensation unit 4129 outputs a color difference image signal including the corrected B-G signal to the B-G correlation discrimination unit 4122 and the B-G interpolation direction discrimination unit 4123. Accuracy of the motion vector is set to accuracy of one pixel.

To be specific, the color difference motion compensation unit 4129 performs a processing of embedding a color difference signal of the past frame into a pixel position where a color difference signal of the current frame is missed based on the motion vector information, as illustrated in FIGS. 19 to 21, in regard to the correction of the B-G signal. FIGS. 19 to 21 are schematic diagrams for describing demosaicing processing performed by the processor according to the second embodiment. Herein, the color difference signal of the past frame is represented by (B-G)p in FIGS. 19 to 21.

Vx(x,y) of Motion Vector is Odd Number, and Vy(x,y) is Even Number Including Zero In this case, color difference signals (B-G)p(k−1,l) and (B-G)p(k+1,l) of the past frame, compensated using each motion vector corresponding to each pixel position between B-G (k−1,l−1) and B-G (k−1,l+1) and between B-G (k+1,l−1) and B-G (k+1,l+1), are inserted as illustrated in FIG. 19.

Vx(x,y) of Motion Vector is Even Number Including Zero, and Vy(x,y) is Odd Number In this case, color difference signals (B-G)p(k,l−1) and (B-G)p(k,l+1) of the past frame, compensated using each motion vector corresponding to each pixel position between B-G (k−1,l−1) and B-G (k+1,l−1) and between B-G (k−1,l+1) and B-G (k+1,l+1), are inserted as illustrated in FIG. 20.

Motion Vector Vx(x,y) is Odd Number, and Vy(x,y) is Odd Number

In this case, a color difference signal (B-G)p(k,l) of the past frame, compensated using a motion vector corresponding to the pixel (k,l) of interest, is inserted as illustrated in FIG. 21.

Vx(x,y) and Vy(x,y) of Motion Vector are Values Other Than Above-Described Values Vertical and horizontal components of the motion vector are values other than the above-described values, arrangement of the color difference signal of the past frame becomes the same as arrangement of the color difference signal illustrated in FIG. 10, and the color difference signal (B-G)p of the past frame is not inserted into surrounding pixels including the pixel (k,l) of interest.

Regarding a signal of a frame which is two frames before the current frame, it is possible to insert much more missing color difference signals at positions of the pixel (k,l) of interest and surrounding pixels thereof if using the motion vector of the immediately previous frame, the motion vector of the current frame, and a color difference signal of the frame which is two frames before the current frame, that has been stored in the past color difference storage unit 412f. An insertion pattern of the color difference signal is a combination of at least two of insertion patterns illustrated in FIGS. 19 to 21.

FIG. 22 is a schematic diagram for describing another example of the demosaicing processing performed by the processor according to the second embodiment. Of course, it is also possible to embed all the missing color difference signal at positions of the pixel (k,l) of interest and surrounding pixels thereof, as illustrated in FIG. 22, if it is possible to use a color difference signal of a frame, which is N frames before the current frame (N is an integer of two or more) and motion vectors of the respective frames up to the frame which is N frames before the current frame. When the motion compensation is performed using the motion vectors of the respective frames up to the frame which is N frames before the current frame, a color difference signal to be inserted at the same position is preferably the color difference signal (B-G)p that is close to the current frame in a time-series manner.

As described above, the color difference motion compensation unit 4129 outputs the color difference image signal including the motion-compensated B-G signal into which the color difference signal (B-G)p of the past frame has been inserted to the B-G correlation discrimination unit 4122 and the B-G interpolation direction discrimination unit 4123, and outputs insertion position determination information (index to discriminate the pattern or the like illustrated in FIGS. 19 to 21), which indicates any pixel position into which the color difference signal (B-G)p has been inserted, to the B-G correlation discrimination unit 4122.

When acquiring the color difference image signal and the insertion position determination information from the color difference motion compensation unit 4129, the B-G correlation discrimination unit 4122 performs the process of determining the direction with the highest correlation as described above.

Vx(x,y) of Motion Vector is Odd Number, and Vy(x,y) is Even Number Including Zero The B-G correlation discrimination unit 4122 calculates a correlation value Sh in the horizontal direction based on the following Formula (9) in addition to the correlation values Ss and Sb that have been described in the first embodiment, for example. The horizontal direction indicates the right-and-left direction in the pixel arrangement illustrated in FIG. 3.

$$Sh = |(B\text{-}G)p(k-1,l) - (B\text{-}G)p(k+1,l)| \qquad (9)$$

The B-G correlation discrimination unit 4122 selects a smallest correlation value and a second smallest correlation value among the correlation values Ss, Sb and Sh. The B-G correlation discrimination unit 4122 determines a direction corresponding to the smallest correlation value as the direction with the highest correlation when an absolute value of a difference between the two selected correlation values is larger than a threshold, and determines that there is no correlation in a specific direction when the absolute value of the difference is smaller than the threshold. The B-G correlation discrimination unit 4122 outputs determination information, which indicates any determination result of "the obliquely upward direction", "the obliquely downward direction", "the horizontal direction", and "no correlation in a specific direction", to the B-G interpolation direction discrimination unit 4123.

Vx(x,y) of Motion Vector is Even Number Including Zero, and Vy(x,y) is Odd Number The B-G correlation discrimination unit 4122 calculates a correlation value Sv in the vertical direction based on the following Formula (10) in addition to the correlation values Ss and Sb that have been described in the first embodiment, for example. The vertical direction indicates the up-and-down direction in the pixel arrangement illustrated in FIG. 3.

$$Sv = |(B\text{-}G)p(k,l-1) - (B\text{-}G)p(k,l+1)| \qquad (10)$$

The B-G correlation discrimination unit 4122 selects a smallest correlation value and a second smallest correlation value among the correlation values Ss, Sb and Sv. The B-G correlation discrimination unit 4122 determines a direction corresponding to the smallest correlation value as the direction with the highest correlation when an absolute value of a difference between the two selected correlation values is larger than a threshold set in advance, and determines that there is no correlation in a specific direction when the absolute value of the difference is smaller than the threshold. The B-G correlation discrimination unit 4122 outputs determination information, which indicates any determination result of "the obliquely upward direction", "the obliquely downward direction", "the vertical direction", and "no correlation in a specific direction", to the B-G interpolation direction discrimination unit 4123.

Motion Vector Vx(x,y) is Odd Number, and Vy(x,y) is Odd Number

The B-G correlation discrimination unit 4122 calculates each correlation value in the obliquely upward direction and the obliquely downward direction using, for example, the color difference signal of the current frame and the color difference signal of the past frame. To be specific, the B-G correlation discrimination unit 4122 calculates a correlation value Ssp in the obliquely upward direction based on the following Formula (11).

$$Ssp = |B-G(k-1, l+1) - (B-G)p(k, l)| + \qquad (11)$$
$$|B-G(k+1, l-1) - (B-G)p(k, l)|$$

In addition, the B-G correlation discrimination unit 4122 calculates a correlation value Sbp in the obliquely downward direction based on the following Formula (12).

$$Sbp = |B-G(k-1, l-1) - (B-G)p(k, l)| + \qquad (12)$$
$$|B-G(k+1, l+1) - (B-G)p(k, l)|$$

The B-G correlation discrimination unit 4122 determines a direction corresponding to a smaller correlation value as the direction with the highest correlation when an absolute value |Ssp−Sbp| of a difference between the correlation values Ssp and Sbp is larger than a threshold, and determines that there is no correlation in a specific direction when the difference absolute value |Ssp−Sbp| is smaller than the threshold. The B-G correlation discrimination unit 4122 outputs determination information, which indicates any determination result of "the obliquely upward direction", "the obliquely downward direction", and "no correlation in a specific direction", to the B-G interpolation direction discrimination unit 4123.

Similarly, when color difference signals have been embedded at all pixel positions using the past color difference signals as illustrated in FIG. 22, the B-G correlation discrimination unit 4122 calculates each correlation value of four directions ("the obliquely upward direction", "the obliquely downward direction", "the horizontal direction" and "the vertical direction"). When this difference absolute value is larger than a threshold, the B-G correlation discrimination unit 4122 determines that the direction with a smallest correlation value is the direction with the highest correlation. In addition, when the difference absolute value is smaller than the threshold, the B-G correlation discrimination unit 4122 determines that there is no correlation in a specific direction. In this case, the B-G correlation discrimination unit 4122 outputs determination information, which indicates any determination result of "the obliquely upward direction", "the obliquely downward direction", "the horizontal direction", "the vertical direction", and "no correlation in a specific direction", to the B-G interpolation direction discrimination unit 4123.

The B-G interpolation direction discrimination unit 4123 calculates an interpolated color difference signal value B-G (k,l) of the B-G signal at the pixel (k,l) of interest based on any formula among the following Formulas (13) to (17) using the determination information from the B-G correlation discrimination unit 4122 and the color difference signal value of the B-G signal including the color difference signal of the past frame.

Determination Information is "Obliquely Upward Direction"

In a case where the determination information is "the obliquely upward direction", the B-G interpolation direction discrimination unit 4123 calculates the interpolated color difference signal value B-G (k,l) of the B-G signal at the pixel (k,l) of interest based on the following Formula (13).

$$B\text{-}G(k,l)=\{B\text{-}G(k-1,l+1)+B\text{-}G(k+1,l-1)\}/2 \quad (13)$$

Determination Information is "Obliquely Downward Direction"

In a case where the determination information is "the obliquely downward direction", the B-G interpolation direction discrimination unit 4123 calculates the interpolated color difference signal value B-G (k,l) of the B-G signal at the pixel (k,l) of interest based on the following Formula (14).

$$B\text{-}G(k,l)=\{B\text{-}G(k-1,l-1)+B\text{-}G(k+1,l+1)\}/2 \quad (14)$$

Determination Information is "Vertical Direction"

In a case where the determination information is "the vertical direction", the B-G interpolation direction discrimination unit 4123 calculates the interpolated color difference signal value B-G (k,l) of the B-G signal at the pixel (k,l) of interest based on the following Formula (15).

$$B\text{-}G(k,l)=\{(B\text{-}G)p(k,l-1)+(B\text{-}G)p(k,l+1)\}/2 \quad (15)$$

Determination Information Is "Horizontal Direction"

In a case where the determination information is "the horizontal direction", the B-G interpolation direction discrimination unit 4123 calculates the interpolated color difference signal value B-G (k,l) of the B-G signal at the pixel (k,l) of interest based on the following Formula (16).

$$B\text{-}G(k,l)=\{(B\text{-}G)p(k-1,l)+(B\text{-}G)p(k+1,l)\}/2 \quad (16)$$

Determination Information Is "No Correlation in Specific Direction"

In a case where the determination information is "no correlation in a specific direction", the B-G interpolation direction discrimination unit 4123 calculates the interpolated color difference signal value B-G (k,l) of the B-G signal at the pixel (k,l) of interest based on the following Formula (17).

$$B-G(k,l) = \{B-G(k-1,l+1)+B-G(k+1,l-1)+ \\ B-G(k-1,l-1)+B-G(k+1,l+1)\}/4 \quad (17)$$

Although the interpolation is performed using an average value of the B-G signals of four surrounding pixels in the above-described Formula (17), the interpolation may be performed using the B-G signals of sixteen surrounding pixels or more with which a high spatial frequency can be maintained.

The B-G interpolation direction discrimination unit 4123 outputs a color difference signal relating to a color difference B-G in which the B-G signals including the interpolated color difference signal, obtained by calculation of the interpolated color difference signal value B-G (k,l) with respect to the pixel (k,l) of interest, are arranged in a checkerboard pattern to the B-G interpolation unit 4124. Hereinafter, the display image signal is generated in the image processing unit 41 in the same manner as in the above-described first embodiment.

In addition, the direction-discriminating interpolation processing using information of the past frame may be performed for the R-G signal, similarly to the above-described B-G signal.

In the interpolation processing, the motion detection for each pixel is performed at an input stage (the pre-processing unit 411a) of the interpolation processing unit 412d, which makes it possible to use the results of the motion detection to determine the direction-discriminating interpolation of the color difference signal performed by the interpolation processing unit 412d. Needless to say, the motion detection processing for each pixel may be performed in the interpolation processing unit 412d.

Figure 23:
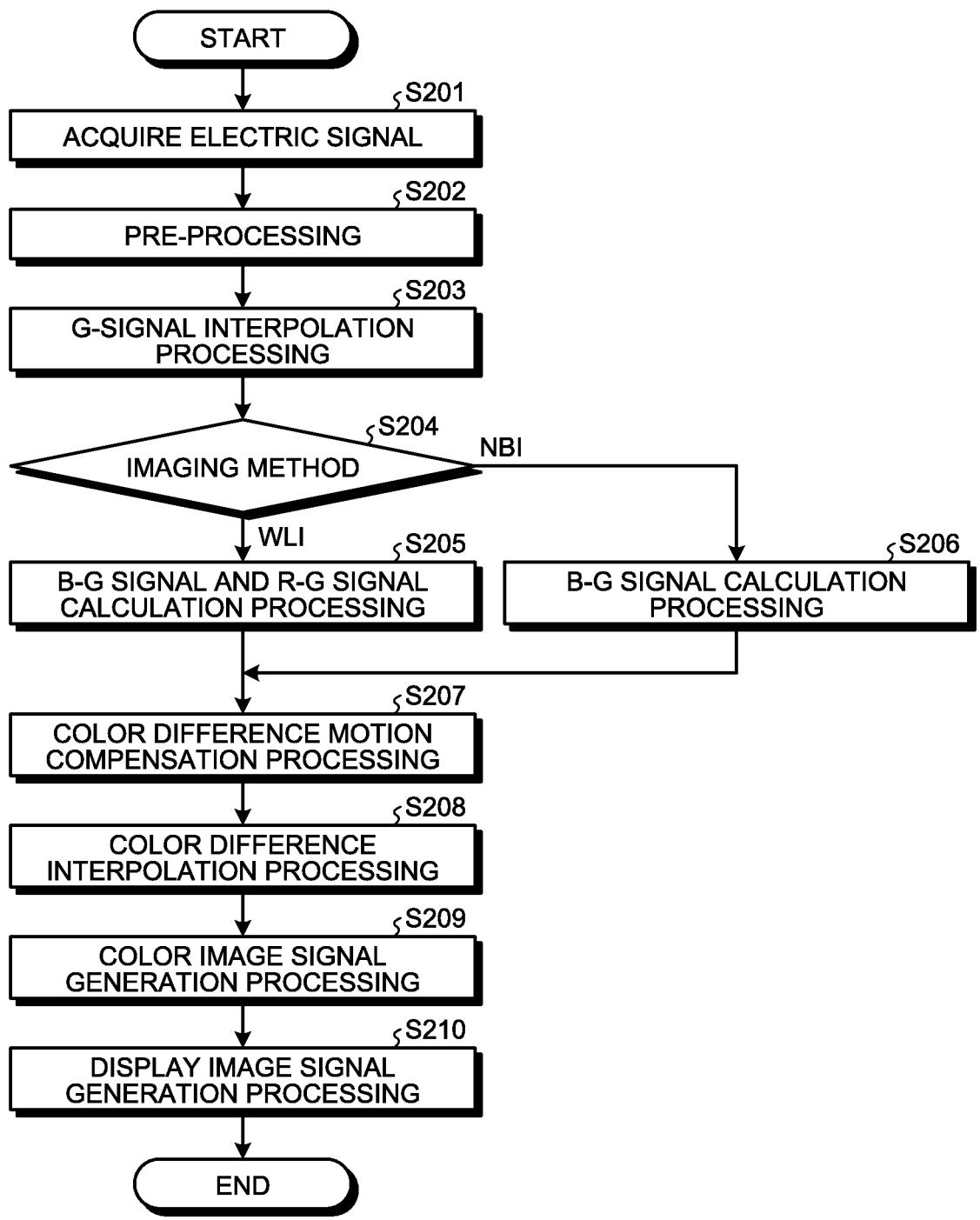
FIG. 23 is a flowchart for describing signal processing which is performed by the processor according to the second embodiment of the present invention.

Next, the signal processing performed by the processor 4a will be described with reference to the drawings. FIG. 23 is a flowchart for describing signal processing which is performed by the processor according to the second embodiment. When acquiring an electric signal from the endoscope 2 (distal end portion 24), the processor 4a performs the same processes as the processes of steps S101 to S106 in the above-described first embodiment to generate a pixel value and an interpolated value of a G component and a signal value of a color difference image signal (steps S201 to S206). In the pre-processing in step S202, the process of detecting the motion vector for each pixel is performed by the motion compensation unit 4115.

The color difference interpolation unit 412e performs color difference motion compensation processing based on the color difference image signal acquired by the G-interpolated color difference calculation unit 412a (step S207). To be specific, the past color difference separation unit 4128 acquires the color difference image signal of the immediately previous frame by referring to the past color difference storage unit 412f, and extracts and outputs only the B-G signal to the color difference motion compensation unit 4129. The color difference motion compensation unit 4129 performs the correction (color difference motion compensation processing) of the B-G signal based on the motion vector information output from the pre-processing unit 411a, a B-G signal as a color difference signal of the past frame output from the past color difference separation unit 4128, and a B-G signal of the current frame output from the color difference separation unit 4121. The color difference motion compensation unit 4129 outputs a color difference image signal including the corrected B-G signal to the B-G correlation discrimination unit 4122 and the B-G interpolation direction discrimination unit 4123.

When the B-G signal is corrected by the color difference motion compensation unit 4129, the color difference interpolation unit 412e performs the color difference interpolation processing based on the color difference image signal that has been acquired from the G-interpolated color difference calculation unit 412a and the B-G signal that has been corrected by the color difference motion compensation unit 4129 (step S208).

The color image signal generation unit 412c generates a color image signal forming a color image using the pixel value and the interpolated value of the G component generated by the G-interpolated color difference calculation unit 412a, and a signal value of the color difference image signal generated by the color difference interpolation unit 412e (step S209). To be specific, the color image signal generation unit 412c generates an RGB signal or a GB signal by adding the G signal or the interpolated G signal and the color difference signal (the B-G signal or the R-G signal) at each pixel position, and outputs the generated signal to the display image generation processing unit 413 as the color image signal.

The display image generation processing unit 413 executes the gradation conversion, magnification processing, the structure enhancement processing for the structures such as the capillaries of the mucosal superficial portion and the mucosal fine patterns, and the like with respect to the color image signal generated by the color image signal generation unit 412c, to generate the display image signal for display (step S210). After executing the predetermined processing, the display image generation processing unit 413 outputs the processed signal to the display unit 5 as the display image signal.

According to the above-described second embodiment, it is possible to obtain the same effect of the first embodiment. Further, the endoscope apparatus capable of switching between the WLI and the NBI is configured to determine a higher-correlation direction using the B-G signals corresponding to the current frame and the past frame in time with respect to the B-G signal at the pixel position of interest and to perform the interpolation using the B-G signal in the determined higher-correlation direction. Thus, it is possible to perform the interpolation also relating to the capillaries of the mucosal superficial portion, blood vessels in a mucosal middle layer, and blood vessels in a mucosal deep layer in a direction along a blood vessel travel route, and particularly, to more reliably maintain resolving power of the B-G signal in the NBI.

In the first and second embodiments, the color filter 202a including the plurality of filters each of which passes light of the predetermined wavelength band is provided on the light receiving surface of the image sensor 202. However, the filters may be individually provided for each pixel of the image sensor 202.

The endoscope apparatuses 1 and 1b according to the first and second embodiments perform switching of the illumination light, emitted from the illumination unit 31 depending on the insertion or removal of the switching filter 31c or the rotation of the rotation filter 31g, to any light between the white illumination light and the narrow band illumination light, with respect to the white illumination light emitted from the single light source 31a. However, two light sources that emit the white illumination light and the narrow band illumination light, respectively, may be switched to emit any of the white illumination light and the narrow band illumination light. When the two light sources are switched to emit any of the white illumination light and the narrow band illumination light, the invention can be also applied to a capsule endoscope which includes, for example, a light source unit, a color filter, and an image sensor and is introduced into a subject.

In the first and second embodiments and modified example, the A/D converter 205 is provided at the distal end portion 24 in the endoscope apparatuses 1 to 1b. However, the A/D converter 205 may be provided in the processor 4 or 4a. In addition, the configuration relating to the image processing may be provided in the endoscope 2, a connector that connects the endoscope 2 and the processor 4, the operating unit 22, and the like. In the above-described endoscope apparatuses 1 to 1b, the endoscope 2 connected to the processor 4 or 4a is identified using the identification information or the like stored in the imaging information storage unit 206. However, an identification unit may be provided in a connecting part (connector) between the processor 4 or 4a and the endoscope 2. For example, a pin for identification (the identification unit) is provided on the endoscope 2 side to identify the endoscope 2 connected to the processor 4.

In the first and second embodiments, the G-interpolated color difference calculation unit 412a performs the interpolation on the pixel (the R pixel or the B pixel) where the G signal is missed, based on the surrounding pixels to generate the G-interpolated signal. However, linear interpolation in which interpolation processing is performed by discriminating an interpolation direction may be used, or interpolation processing may be performed using cubic interpolation or other non-linear interpolation.

In the first and second embodiments, the color filter 202a is configured by arraying the filter units U1 having the Bayer array in a matrix, but the array is not limited to the Bayer array. For example, a filter unit having a filter array in which the density of G components is higher than that of B components may be used in the case of switching between the WLI and the above-described NBI. Any filter array can be applied as long as it is the filter array in which the density of pixels to generate an electric signal of a luminance component of the white illumination light is higher than the density of pixels to generate an electric signal of a luminance component of the narrow band illumination light.

Although, in the first and second embodiments, the exemplary endoscope apparatus including the image processing apparatus is employed, an imaging apparatus for performing image processing, such as a microscope apparatus, may be employed.

According to some embodiments, it is possible to obtain the high-resolution image in any of the white light imaging and the narrow band imaging.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for processing electric signals generated by an image sensor, the electric signals comprising:

an electric signal of a first luminance component generated at each of first pixels of the image sensor;

an electric signal of a second luminance component generated at each of second pixels of the image sensor; and an electric signal of a third luminance component generated at each of third pixels of the image sensor, wherein the first pixels, second pixels and third pixels are arranged to sense incoming light passed through filter units arranged in a color filter array where each of the filter units comprises two filters for the first luminance component being diagonally arranged, and a filter for the second luminance component and a filter for the third luminance component being diagonally arranged, and wherein in the image processing apparatus comprises a processor comprising hardware, wherein the processor is configured to:

for each of the second pixels, interpolate electric signal of the first luminance component for the each of the second pixels based on the electric signal of the first luminance component generated by the first pixels surrounding the each of the second pixels to generate an interpolated electric signal of the first luminance component for the each of the second pixels; and for the each of the second pixels, calculate a difference between the interpolated electric signal of the first luminance component for the each of the second pixels and the electric signal of the second luminance component generated at the each of the second pixels to generate a color difference signal for the each of the second pixels;

discriminate an interpolation direction from one of an obliquely upward interpolation direction and an obliquely downward interpolation direction for interpolating a missing color difference signal for one of the third pixels based on the color difference signals for the second pixels surrounding the one of the third pixels;

interpolate the missing color difference signal for the one of the third pixels based on the color difference signals for the second pixels along the interpolation direction discriminated; and generate an electric signal of the first color component for the one of the third pixels based on the missing color difference signal interpolated for the one of the third pixels.

2. The image processing apparatus according to claim 1, wherein the first pixels are configured to receive green wavelength band light to generate the electric signal of a green component as the first luminance component, and wherein the second pixels are configured to receive blue wavelength band light to generate the electric signal of a blue component as the second luminance component, and wherein the third pixels are configured to receive red wavelength band light to generate the electric signal of a red component as the third luminance component.

3. The image processing apparatus according to claim 1, wherein the processor is configured to:

for each of a plurality of interpolation direction candidates, calculate a correlation value for the each of a plurality of interpolation direction candidates based on the color difference signals for the second pixels surrounding the one of the third pixels in a direction of the each of the plurality of interpolation direction candidates; and discriminate, as the interpolation direction, one of the plurality of interpolation direction candidates based on the correlation values for the plurality of interpolation direction candidates calculated.

4. The image processing apparatus according to claim 1, wherein the processor is configured to:

detect, as a motion vector, a motion between a first motion detection image and a second motion detection image by using the first motion detection image and the second motion detection image, the first motion detection image being based on an image signal of a past frame temporally before a frame to be interpolated, the second motion detection image being based on an image signal of the frame to be interpolated;

embed a past-frame color difference signal for the past frame in the image signal of the frame to be interpolated based on the motion vector; and interpolate the missing color difference signal for the one of the third pixels based on the interpolation direction discriminated and the past-frame color difference signal.

5. A system comprising:

a light source configured to emit white illumination light or narrow band illumination light, the white illumination light including red wavelength band light, green wavelength band light and blue wavelength band light, and the narrow band illumination light having a narrower wavelength band than wavelength bands of the white illumination light;

the color filter array;

the image sensor; and the image processing apparatus according to claim 1.

6. An image processing method for processing electric signals generated by an image sensor, the electric signals comprising:

an electric signal of a first luminance component generated at each of first pixels of the image sensor;

an electric signal of a second luminance component generated at each of second pixels of the image sensor; and an electric signal of a third luminance component generated at each of third pixels of the image sensor, wherein the first pixels, second pixels and third pixels are arranged to sense incoming light passed through filter units arranged in a color filter array where each of the filter units comprises two filters for the first luminance component being diagonally arranged, and a filter for the second luminance component and a filter for the third luminance component being diagonally arranged, and wherein the image processing method comprises:

for each of the second pixels, interpolating electric signal of the first luminance component for the each of the second pixels based on the electric signal of the first luminance component generated by the first pixels surrounding the each of the second pixels to generate an interpolated electric signal of the first luminance component for the each of the second pixels; and for the each of the second pixels, calculating a difference between the interpolated electric signal of the first luminance component for the each of the second pixels and the electric signal of the second luminance component generated at the each of the second pixels to generate a color difference signal for the each of the second pixels;

discriminating an interpolation direction from one of an obliquely upward interpolation direction and an obliquely downward interpolation direction for interpolating a missing color difference signal for one of the third pixels based on the color difference signals for the second pixels surrounding the one of the third pixels;

interpolating the missing color difference signal for the one of the third pixels based on the color difference signals for the second pixels along the interpolation direction discriminated; and generating an electric signal of the first color component for the one of the third pixels based on the missing color difference signal interpolated for the one of the third pixels.

7. A non-transitory computer-readable recording medium with an executable program stored thereon for processing electric signals generated by an image sensor, the electric signals comprising:

an electric signal of a first luminance component generated at each of first pixels of the image sensor;

an electric signal of a second luminance component generated at each of second pixels of the image sensor; and an electric signal of a third luminance component generated at each of third pixels of the image sensor, wherein the first pixels, second pixels and third pixels are arranged to sense incoming light passed through filter units arranged in a color filter array where each of the filter units comprises two filters for the first luminance component being diagonally arranged, and a filter for the second luminance component and a filter for the third luminance component being diagonally arranged, and wherein the program causes a computer to at least perform:

for each of the second pixels, interpolating electric signal of the first luminance component for the each of the second pixels based on the electric signal of the first luminance component generated by the first pixels surrounding the each of the second pixels to generate an interpolated electric signal of the first luminance component for the each of the second pixels; and for the each of the second pixels, calculating a difference between the interpolated electric signal of the first luminance component for the each of the second pixels and the electric signal of the second luminance component generated at the each of the second pixels to generate a color difference signal for the each of the second pixels;

discriminating an interpolation direction from one of an obliquely upward interpolation direction and an obliquely downward interpolation direction for interpolating a missing color difference signal for one of the third pixels based on the color difference signals for the second pixels surrounding the one of the third pixels;

interpolating the missing color difference signal for the one of the third pixels based on the color difference signals for the second pixels along the interpolation direction discriminated; and generating an electric signal of the first color component for the one of the third pixels based on the missing color difference signal interpolated for the one of the third pixels.

* * * * *